United States Patent [19]

Criss et al.

[11] Patent Number: 5,782,739
[45] Date of Patent: Jul. 21, 1998

[54] RAPID OPTIMIZATION OF STEREOTACTIC RADIOSURGERY USING CONSTRAINED MATRIX INVERSION

[75] Inventors: Thomas B. Criss, Dayton; Jeffery A. Williams, Baltimore, both of Md.

[73] Assignee: The Johns Hopkins University, Baltimore, Md.

[21] Appl. No.: 660,953

[22] Filed: Jun. 12, 1996

Related U.S. Application Data

[60] Provisional application No. 60/000,224 Jun. 14, 1995.
[51] Int. Cl.⁶ .................................................. A61N 5/00
[52] U.S. Cl. .................................................. 600/1; 128/898
[58] Field of Search ................... 600/1–2; 606/130; 128/897–98

[56] References Cited

U.S. PATENT DOCUMENTS 4,815,448  3/1989  Mills ............................................ 600/2

FOREIGN PATENT DOCUMENTS 0228651  10/1985  Germany ............................ 600/1
3739573   6/1989  Germany ............................ 600/1
4024947   2/1992  Germany ............................ 600/1

*Primary Examiner*—John P. Lacyk
*Attorney, Agent, or Firm*—Eugene J. Pawlikowski; Carla Magda Krivak

[57] ABSTRACT

An algorithm applied in the radiological treatment of tumors which minimizes a cost function which is quadratic in the residual between the prescribed dose distribution and the calculated resultant dose. Possible treatment arcs must be stipulated and the algorithm includes an automatic technique for multiple iso-center selection. One overall strategy can be specification of an unrealistically large number of beams (or arcs) and systematic deletion of those beams having the smallest recommended weights until a practical solution is obtained. Tumor, non-tumor, and avoidance areas can be defined. Constrained matrix immersion results in optimum weights and dosage in the treatment of the tumor.

9 Claims, 8 Drawing Sheets

5,782,739

1

RAPID OPTIMIZATION OF STEREOTACTIC RADIOSURGERY USING CONSTRAINED MATRIX INVERSION

STATEMENT OF GOVERNMENTAL INTEREST

The Government has rights in this invention pursuant to Contract No. N00039-94-C-0001 awarded by the Department of the Navy.

This application claims the benefit of U.S. Provisional application No. 60/000,224, filed Jun. 13, 1995.

BACKGROUND OF THE INVENTION

The primary objective of stereotactic radiosurgery is to deliver a maximized dose (cGy) to a targeted tumor with a minimized radiation of surrounding normal tissue. Improving such differential dose delivery to complex volumes may be enhanced with computer optimization. Existing techniques to optimize treatment planning during radiation oncology include linear programming, inverse reconstruction, and simulating annealing. In linear programming the restriction to non-negative beam weights means that no optimized solution will be produced if no true solution exists. Furthermore, in this form of programming clinically desirable objective functions may not be well approximated by linear functions. Inverse construction strategies are generally efficient but they do not necessarily result in optimization of dose deposition. As to the third of the prior art approaches to maximize optimization, in simulated annealing no solution exists unless arbitrary maximum dose values are assigned to normal tissue, target dose points are only randomly sampled, and the time required for optimization becomes prohibitive.

SUMMARY OF THE INVENTION

In the invention of the present application, an algorithm has been developed for three-dimensional treatment planning in a matter which provides a cost function which is quadratic in the residual between the prescribed dose distribution and a calculated resultant dose. The technique has been found to be efficient since it rapidly produces a solution for the required beam weights and ensures that no beam weight is negative.

In general, the present invention uses constrained matrix inversion implemented in Visual Basic and Fortran and running on a PC in the Windows environment. Brain CT files with external BRW fudicials are imported and tumor, non-tumor and avoidance volumes are defined. Possible treatment arcs and iso-centers are stipulated. There is an automatic technique for multiple iso-center selection. Dose volume histograms, dose contour plots and other displays are generated as aids for evaluating the quality of the solution. The speed with which the algorithm can generate a solution enables investigation of many treatment options. It is proposed to adopt a specification of an unrealistically large number of beams (or arcs) and systematically delete those beams having the smallest recommended weights until a practical solution is obtained. To further speed the computation, the program allows deterministic decimation of the data in areas of normal tissue which are distant from the tumor. Even with decimation, as many as 40,000 points are usually calculated. Representative calculation times for 40,000 points on a 486-33 PC are:

2

| # Beams | Problem Initialization (sec) | Solution (sec) |
|---|---|---|
| 50 | 60 | 10 |
| 100 | 300 | 30 |

In accordance with the present invention, solution times will vary depending upon the specific geometry of each case. The results found demonstrate efficient optimization with dense sampling of the target, its neighborhood and the avoidance areas and with deterministic sampling (low order decimation) of the normal tissue.

Considering an exemplary use of the system, the primary objective is to arrive at a radiation dosage prescription of dosage versus beam angle (possibly for multiple iso-centers) to be used to treat tumors in the body. The radiation is introduced into the body via a series of exposures to external beams of either collimated X-rays or Gamma rays. It is proposed to calculate, choose and adjust the direction of incidence of radiation and the intensity of the radiation applied. If it is obvious that the radiation is intended to treat, or destroy, unhealthy tissue such as an internal tumor, it is equally desirable that the radiation itself should not injure healthy tissue. Unfortunately, any beam of radiation directed to an interior point of the human body must necessarily cause some damage to healthy tissue. It is equally evident, moreover, that certain areas of the body must not be subjected to any radiation whatsoever, due to their criticality or acute sensitivity to radiation. One primary object of the invention, consequently, is to introduce radiation into a human body from multiple directions with the beams intersecting at the tumor, thereby concentrating the maximum dosage of radiation to the tumor. It must be recognized, however, that healthy tissue near the point of intersection might still be subject to large doses. By varying the intensities of radiation as a function of angle, it has been found that the damage to healthy tissue and to avoidance areas is minimized. Counter to the present clinical techniques for determining the best dosage prescription by trial and error and assisted only by computer software that calculates the resultant dosage profile, the dosage calculation software of the algorithm as applied in the present invention is best described as a treatment optimization tool. The computer-implemented process of the present invention actually suggests a dosage prescription. It is referred to as a treatment optimization tool to distinguish it from the more limited products presently available, such as manual techniques which often require a contribution of ten hours or more of physician and technician involvement to arrive at a treatment plan. The current invention requires areas of the brain to be manually traced following which the algorithm in a computer-assisted mode prescribes a set of appropriate beam strengths using only a few minutes of computer time.

BRIEF DESCRIPTION OF THE DRAWINGS

In the drawings, which constitute a part of the specification, an exemplary embodiment demonstrating certain objectives and features, is set forth as follows.

DESCRIPTION OF THE PREFERRED EMBODIMENTS

Figure 1:
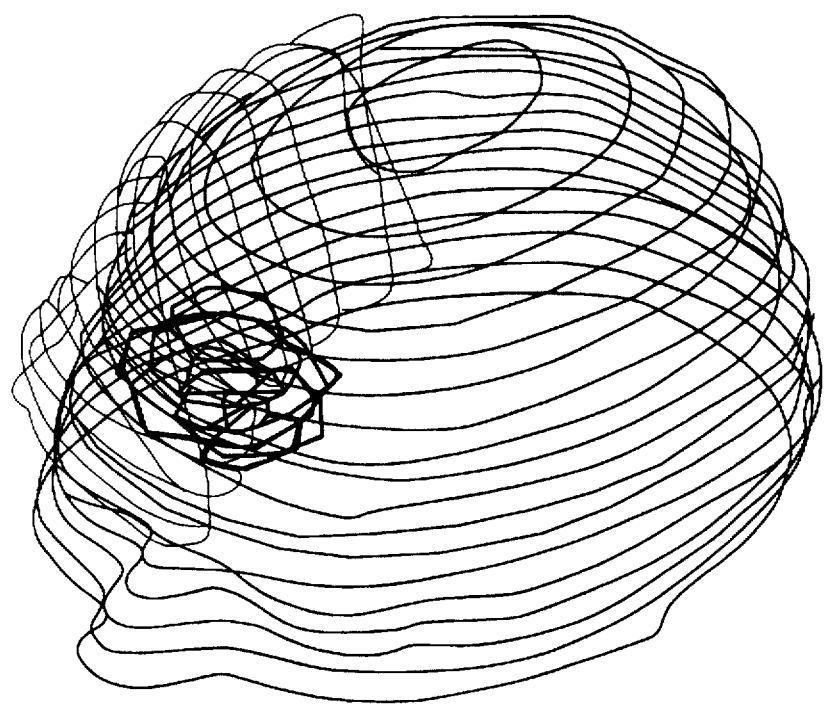
FIG. 1 is a polygon representation of a human brain, based on a CAT scan.

The cost function (the quantity to be minimized) is a weighted sum of the squared residuals between the intended dose and the predicted dose.

$$\text{Cost} = \sum_{i=1}^{\text{Volume\_Elements}} w_i \cdot \left[ \left( \sum_{k=1}^{\text{Number\_of\_Beams}} c_k \cdot d_{i,k} \right) - m_i \right]^2$$

with respect to the $c_k$, subject to the constraint that all $c_k$ be non-negative.

where the index i denotes the range of volume elements (as many as 40,000 points are used in calculations)

the index k denotes the range of beams (i.e., up to several hundred potential beams)

$c_k$ is the relative weight of the k-th beam, which is to be solved for.

$m_i$ is the intended dose in volume element i. These values could be anything, independently for each point, but for simplicity we use zero for normal and avoidance areas, and some constant value for tumor areas.

$w_i$ is the weight with which the residual at point i is to be considered, i.e., the weight of an avoidance area is much higher than the weight for other normal tissue, even though the intended dose for both points is zero. Weights could be individually assigned to each point, but for simplicity, are assigned by tissue type (tumor, healthy, avoidance area)

$d_{ik}$ is the predicted dose at point i that would arrive only from a single unit strength beam number k. This term is where all of the geometry comes in. Any kinds of beams, arcs, multiple iso-centers can be specified and the contribution of each beam to each point deterministically calculated.

The method is able to carry out the optimization without having to permanently store all of the ~few hundred X many thousand values for $d_{ik}$. For example, 500 beams times 40,000 points would be 20 million $d_{ik}$, which would require 80 megabytes to store as single precision.

Also, calculating the optimum requires calculating pairwise products of the $d_{ik}$ at each point which could involve about $40,000 \times 500^2$ calculations, or $10^{10}$ multiples. A method has been developed for reducing the possibilities many-fold in order to speed up the computations.

The optimization is carried out as follows: The derivatives of the cost function with respect to the $c_k$ are calculated and set to zero. This results in k simultaneous linear equations for the unknown $c_k$. If the $c_k$ were solved for using standard techniques of linear algebra, there would be no assurance that all of the $c_k$ were non-negative, which is a physical constraint.

Building upon an iterative technique for solving certain types of matrix equations presented in "Modern Mathematical Analysis" by Murray H. Protter and Charles B. Morrey, Jr., Addition-Wesley, 1966, a new, efficient, iterative technique has been developed that allows constraints to be imposed during the iteration process. The matrix equations arising from this optimization problem can always be put into a form (through suitable transformations) which satisfy the conditions for convergence and stability presented in the reference. Another advantage of the iterative technique for matrix equation solution is that it provides full accuracy using only single precision arithmetic, while more standard techniques become unusable as the matrix rank approaches one hundred unless double precision is used.

A technique has also been developed which automatically analyzes possible linear dependencies in the equations and calculates terms that can be added to the cost function to remove the degeneracies. This could happen if two beams happen to have almost the same signature, e.g., beams from the same angles, but associated with two different iso-centers which happen to lie along the line of sight of the beams. In this case, there would be no physical distinction between the beams, and the presence of two such identical beams would lead to a mathematical degeneracy in the solution.

The detailed computer program listings for carrying out the data processing steps described in this application are set forth in the following appendices A–C.

Appendix A describes main source code definitions for various variables and data structures.

Appendix B contains source code which describes various subroutines for executing the algorithm.

Appendix C contains source code which defines maximum grid and tissue type parameters meant for incorporation into various ones of the subroutines.

The drawings will now be discussed. FIGS. 1–8 are examples of how the present invention works and how it can be used.

FIG. 1 is a wire-frame view of tissue/tumor structures produced by subroutine "THREEDV."

Figure 2:
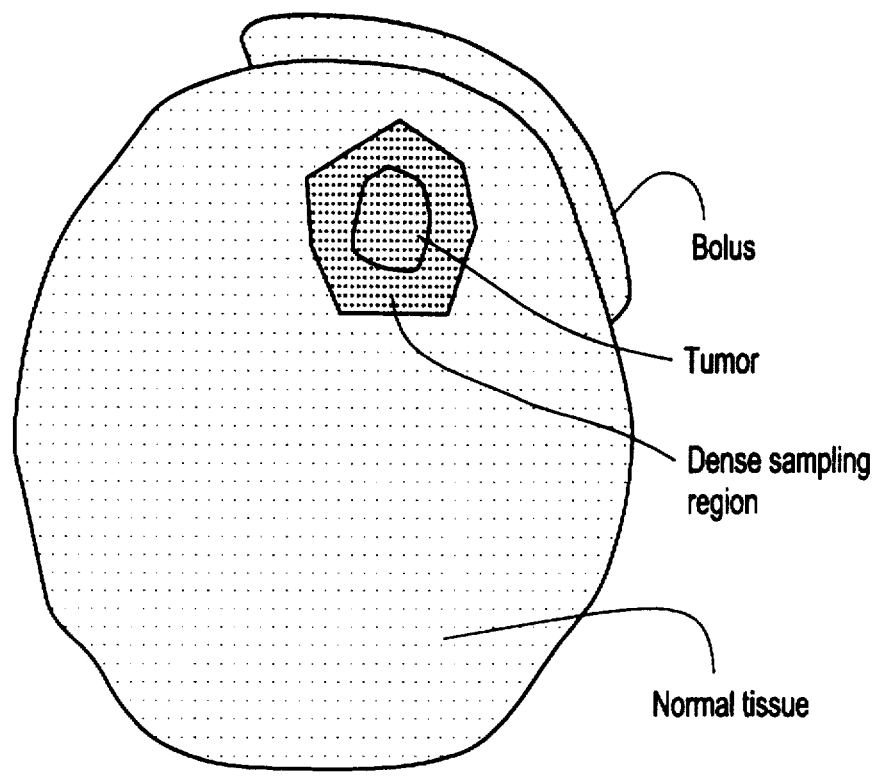
FIG. 2 shows one slice of the data shown in FIG. 1 with the tumor being viewed from a different angle.

FIG. 2 shows the location of evaluation points in one of the slices of the CAT Scan. This figure shows a denser sampling of evaluation points near the tumor.

Figure 3:
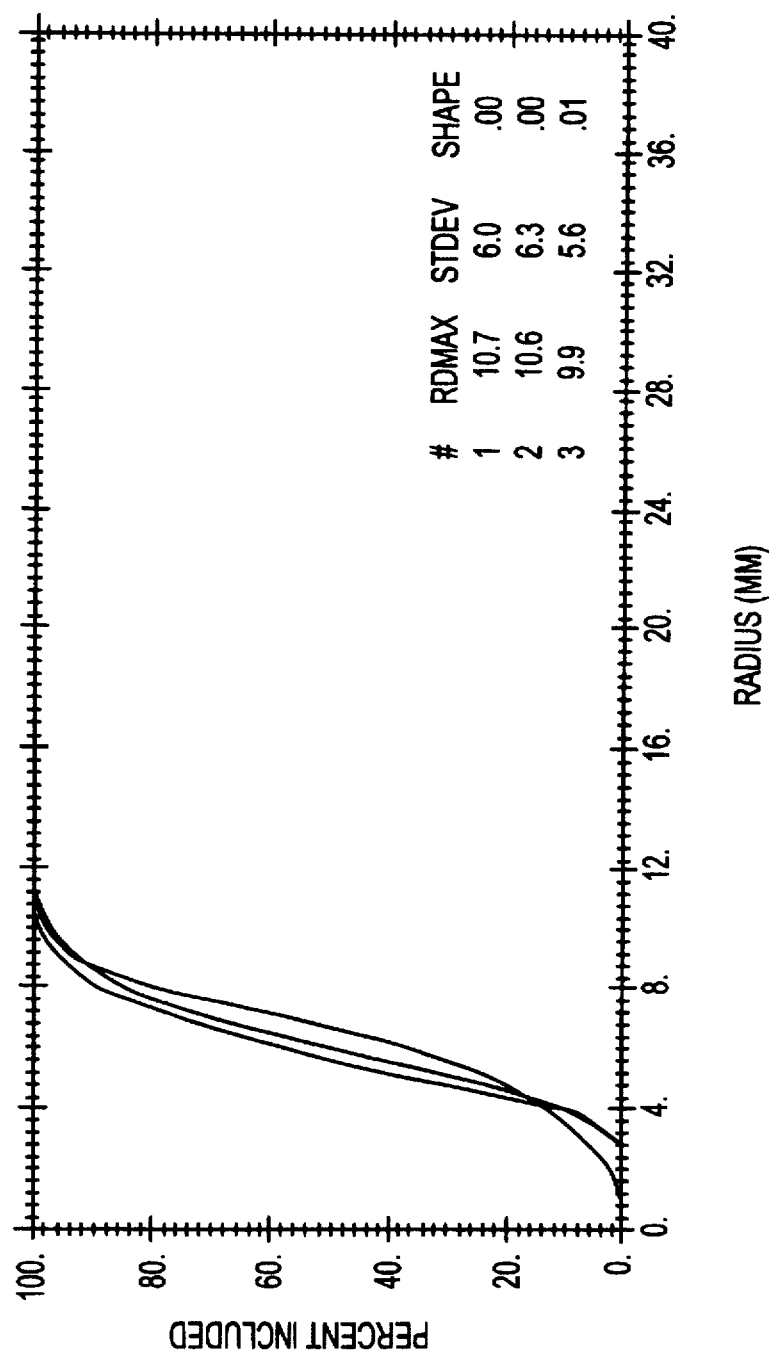
FIG. 3 shows an Iso-center Volume Histogram showing the results of automatic iso-center location and sizing.

FIG. 3 is a plot produced by the subroutine "MAKE_ISO_CENTERS." This plot can be used to evaluate the efficacy of different numbers and placements of multiple ISO-centers.

Figure 4:
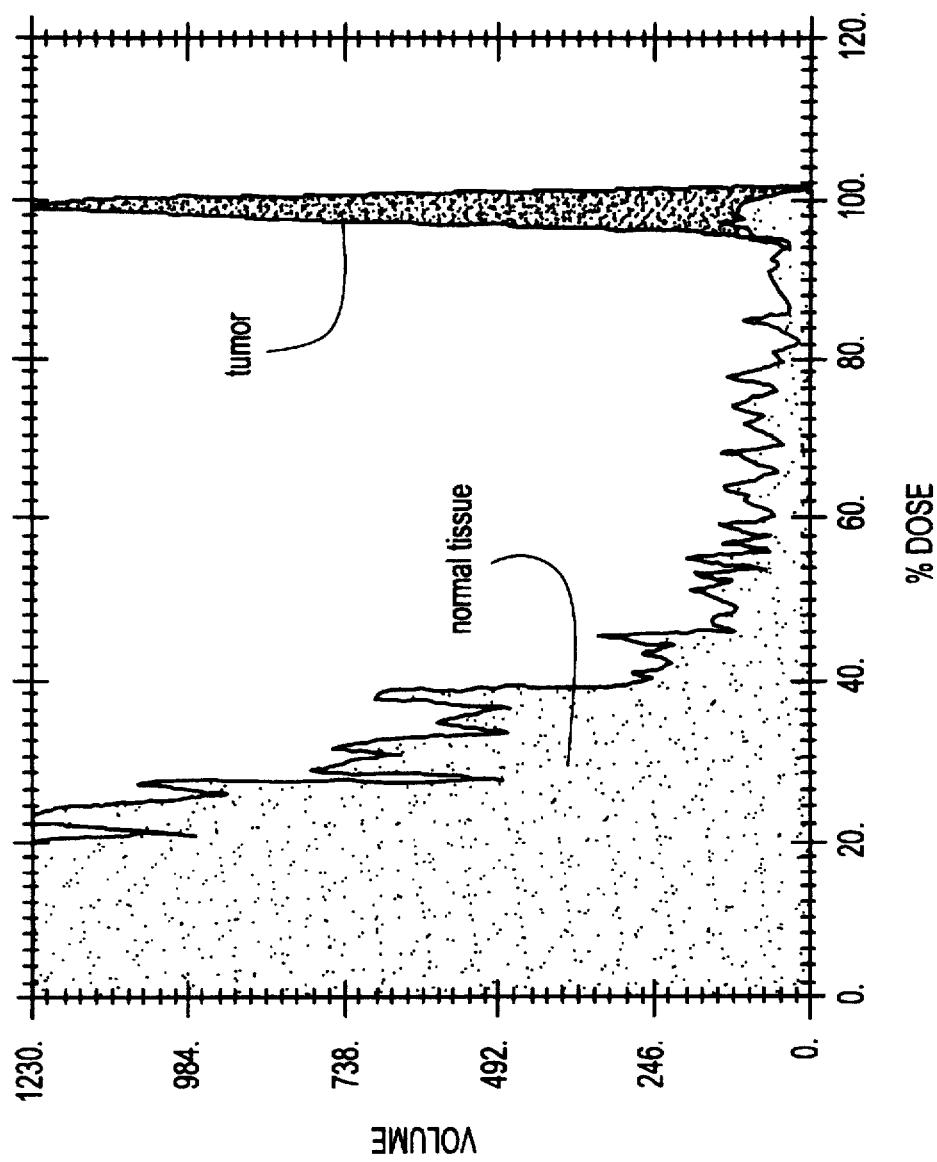
FIG. 4 shows a dose volume histogram and a concentration of almost 100% of the radiation centered on a tumor.

FIG. 4 is a dose volume histogram sample plot showing the amount of dose-to-tumor and to healthy tissue. The dose is determined by subroutines "CALC_DOSE", "DVHIST," "CUMHIST" and "DVH_PLOT."

Figure 5:
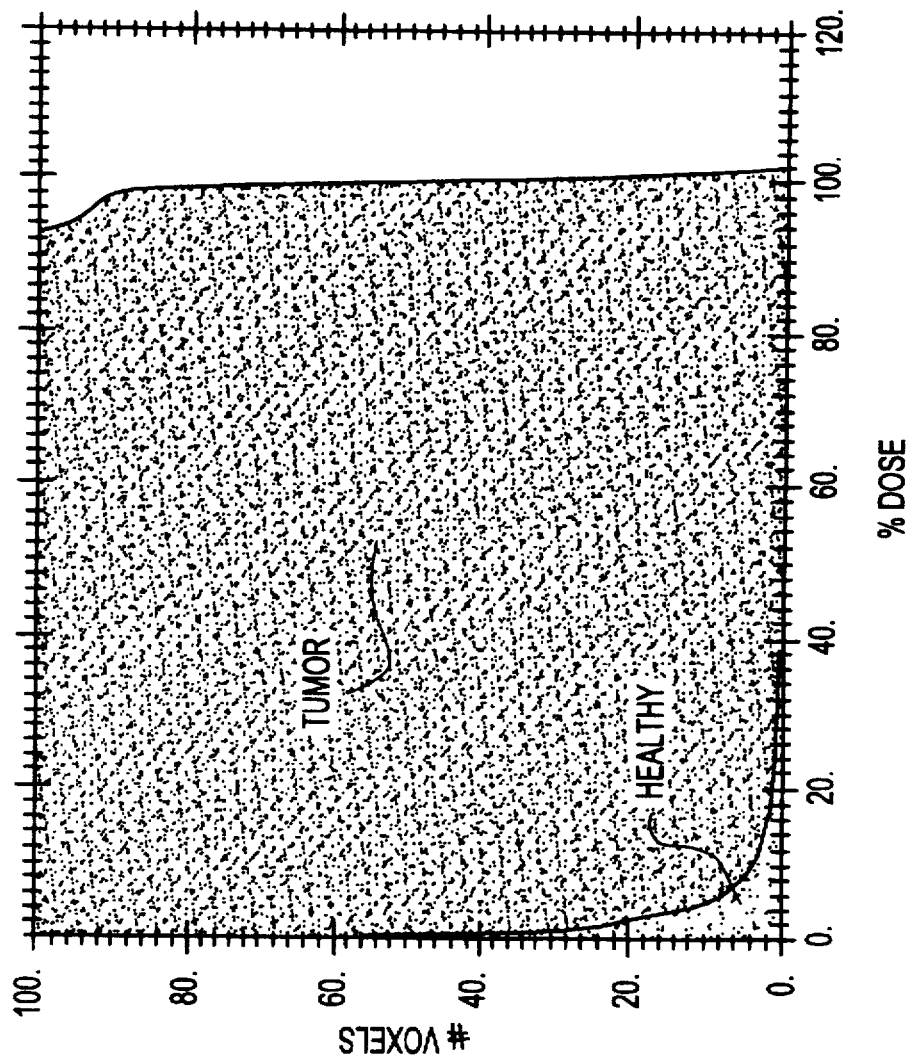
FIG. 5 shows a cumulative dose volume histogram and the diminution of dose volume over nearly all of the region of surrounding healthy tissue.

FIG. 5 is a cumulative dose volume histogram sample plot showing the amount of dose-to-tumor and to healthy tissue. The dose is calculated by subroutine "CALC_DOSE," "DVHIST," "CUMHIST" and "DVH_PLOT."

Figure 6:
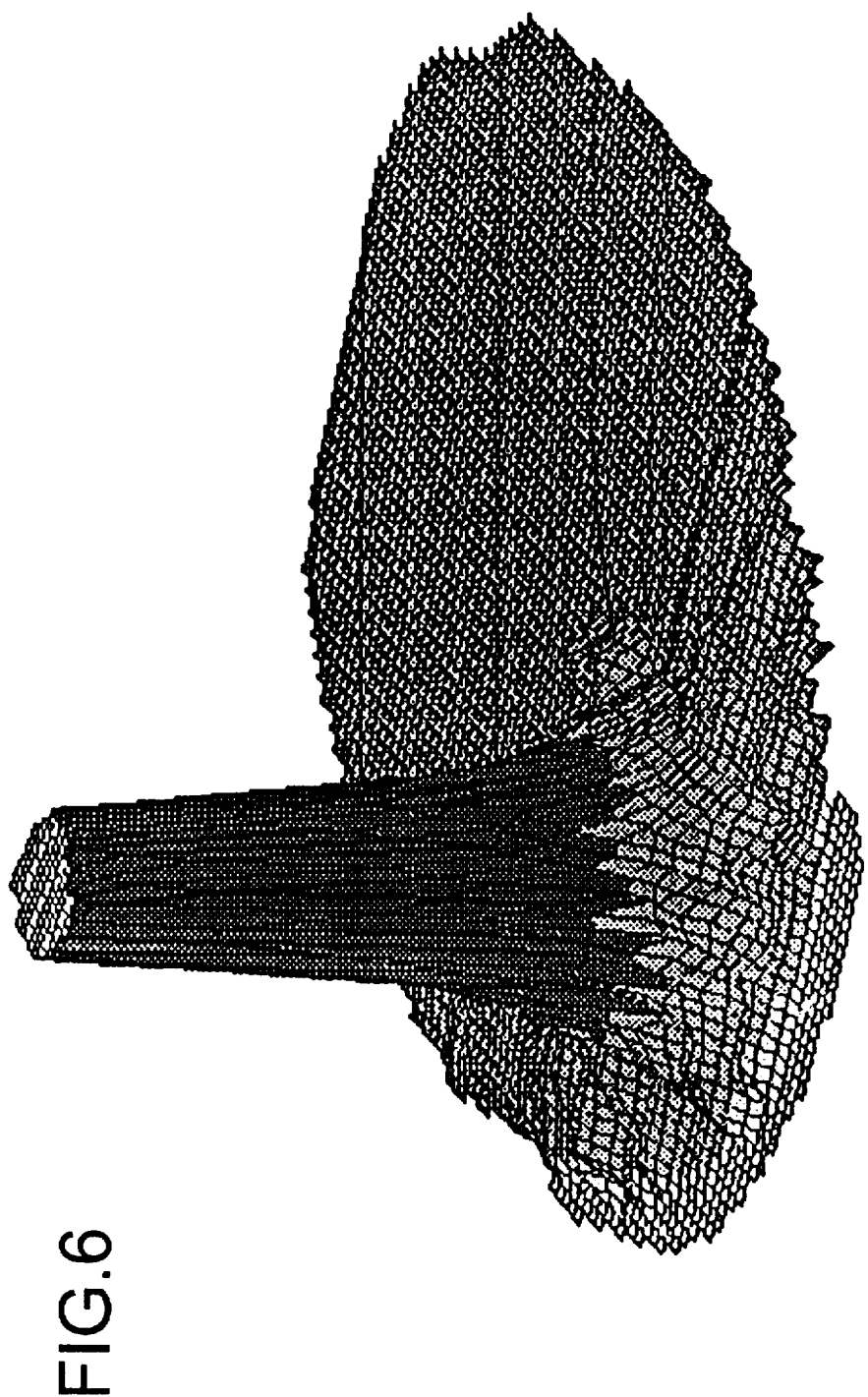
FIG. 6 is a spatial dose distribution in one slice of a CAT scan.

FIG. 6 is a plot showing spatial dose distribution in one tissue slice. The dose distribution is color coded by tissue type. The plot is generated by subroutine "THREEF3X."

Figure 7:
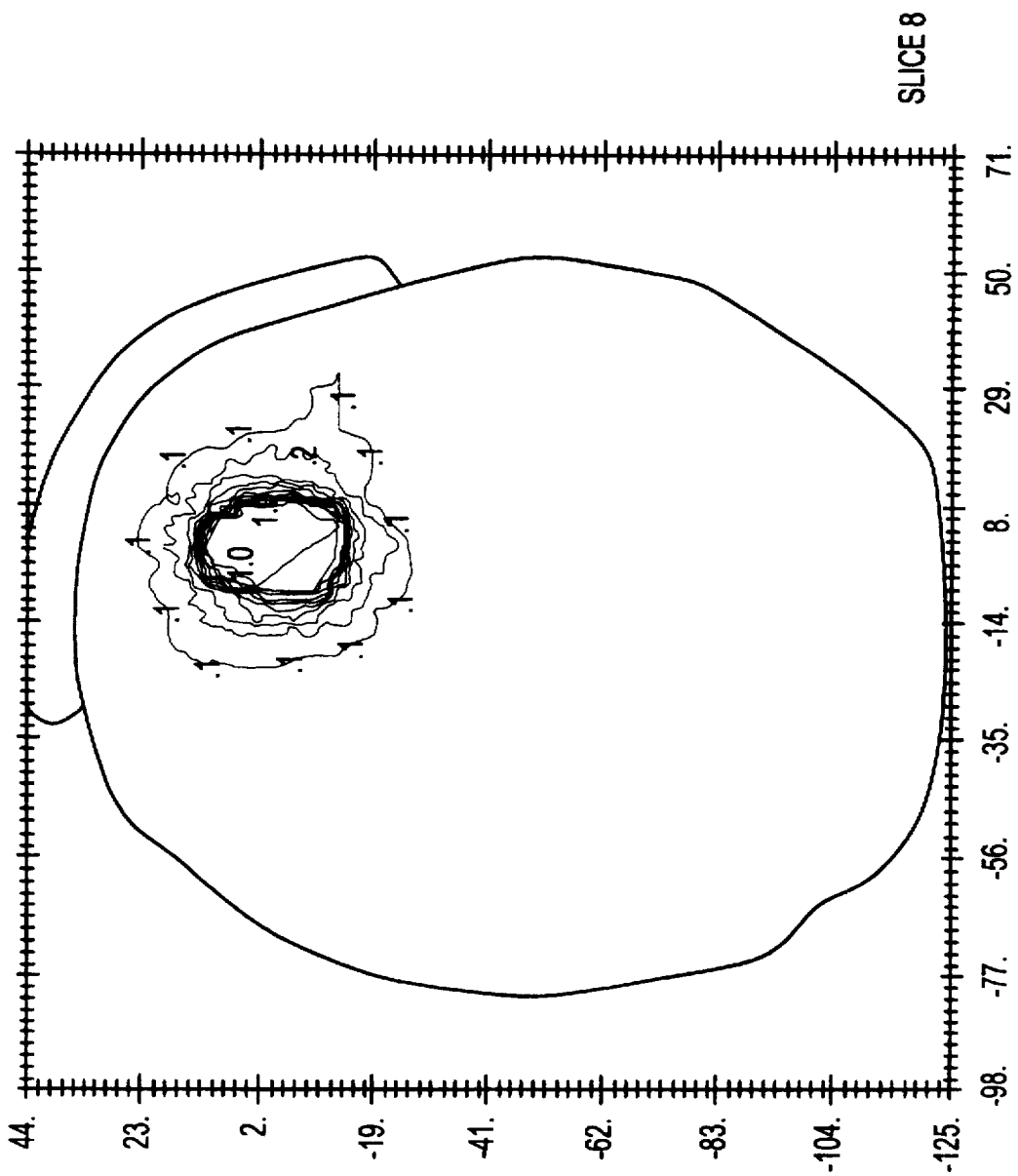
FIG. 7 is a contour plot of the tumor shown in FIG. 6.
Figure 8:
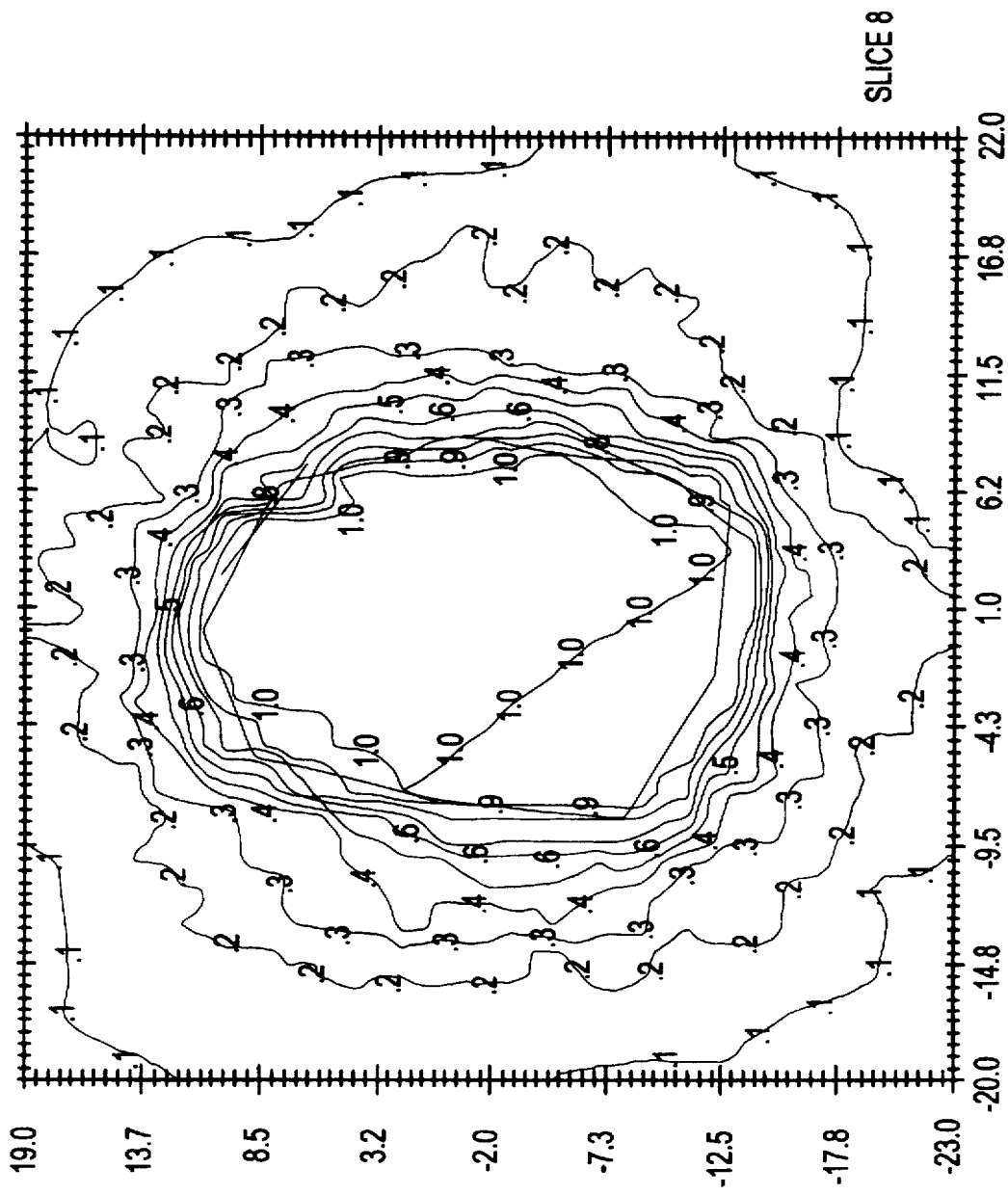
FIG. 8 is a view, greatly enlarged, of the tumor shown in FIG. 7.

FIG. 7 is a contour plot of dosage in one tissue slice. The plot is generated by subroutine "CONTOR3X." FIG. 8 is a zoomed-in contour plot of dosage in one of many slices. The plot is generated by the subroutine "CONTOR3X"

The above and other features of the present invention are illustrative only of preferred embodiments of the present invention, and a variety of modifications and changes may be made therein without departing from the intended scope of the invention.

Appendix A
Source Code Defining Primary Variables and Data Structures

```
*       ----------------------------------------------------------------
        type xray_point         ! INFORMATION ASSOCIATED WITH A DISTINCT VOXEL OF BRAIN TISSUE
          sequence
          real*4      x         ! x coordinate of voxel
          real*4      y         ! y coordinate of voxel
          real*4      z         ! z coordinate of voxel
          real*4      volume    ! volume represented by decimated voxel in mm^3
          real*4      dose      ! calculated 1 mm^3 dose for this voxel
          real*4      sigma     ! relative dosage tolerance within tissue class
          integer*2   index     ! index into tissue information array
          integer*1   tclass    ! TISSUE CLASS: AIR, BOLUS, NORML, TUMOR, AVOID
          integer*1   isocenter ! the iso-center with which this point belongs
        end type
*       ----------------------------------------------------------------

*       ----------------------------------------------------------------
        type xray_boundary      ! 3-D COORDINATES (IN MM) OF A POINT ON A VERTEX
          sequence              ! OF A POLYGON DEFINING THE BOUNDARY OF AN
          real*4      x         ! ORGAN OR TUMOR WITHIN A SLICE OF A CAT SCAN
          real*4      y
          real*4      z
        end type
*       ----------------------------------------------------------------

*       ----------------------------------------------------------------
        type xray_beam              ! INFORMATION ASSOCIATED WITH A DISTINCT INTENDED
          sequence                  ! BEAM OF RADIATION
          integer*4   number        ! flag to restrict all beams in arc to the same dosage
          integer*4   isocenter     ! number of iso-center current beam is associated with real*4      x0            ! X coordinate of iso_center (mm)
          real*4      y0            ! Y coordinate of iso_center (mm)
          real*4      z0            ! Z coordinate of iso_center (mm)

real*4      radius_max    ! maximum radius for current iso-center
          real*4      conesize      ! size of radiation cone OR if < 0.0 implies SILHOUETTE
          real*4      weight        ! optimized beam weight - result of calculation real*4      table_angle   ! INTENDED ENTRY ANGLE OF RADIATION (degrees)
          real*4      gantry_angle  ! INTENDED ENTRY ANGLE OF RADIATION (degrees)
          real*4      collim_angle  ! INTENDED ENTRY ANGLE OF RADIATION (degrees)

real*4      a             ! element of rotation matrix
          real*4      b             ! element of coordinate rotation matrix
          real*4      c             ! element of coordinate rotation matrix
          real*4      d             ! element of coordinate rotation matrix
          real*4      e             ! element of coordinate rotation matrix
          real*4      f             ! element of coordinate rotation matrix
          real*4      g             ! element of coordinate rotation matrix
          real*4      h             ! element of coordinate rotation matrix
          real*4      i             ! element of coordinate rotation matrix
        end type
*       ----------------------------------------------------------------

*       ----------------------------------------------------------------
        type xray_grid      ! STRUCTURE USED TO STORE EITHER BEAM STRENGTH VERSUS CROSS-SECTION
!         SEQUENCE          !                OR BEAM'S-EYE VIEW SKIN DEPTH VERSUS CROSS-SECTION
          real*4   grid(-max_grid:max_grid,-max_grid:max_grid)
        end type
*       ----------------------------------------------------------------
```

1

```
type xray_center     ! STRUCTURE USED TO STORE LOCATION OF ISO-CENTERS
   sequence
   real*4    x0          ! X coordinate of iso_center (mm)
   real*4    y0          ! Y coordinate of iso_center (mm)
   real*4    z0          ! Z coordinate of iso_center (mm)
   real*4    radius_max  ! maximum radius from center to any point in iso-center (mm)
end type type xray_tissues    ! INFORMATION ASSOCIATED WITH EACH TYPE OF TISSUE
   sequence
   real*4    sigma        ! intended relative sigma within tissue class
   integer*2 tclass       ! Tissue Class: AIR, BOLUS, NORML, TUMOR, or AVOID
   integer*2 reserved !
end type integer*2          , allocatable :: voxel(:,:,:)      ! 3-D ARRAY DEFINING BRAIN
                                                      ! STRUCTURE With Respect To
                                                      ! TISSUE/ORGAN TYPE type (xray_beam)   , allocatable :: beam       (:)    ! ARRAY OF ALL RADIATION BEAMS
type (xray_grid)   , allocatable :: beam_depth(:)     ! LOOK-UP TABLE OF RADIATION
                                                      ! FALL-OFF WITH DEPTH type (xray_grid)   , allocatable :: beam_shape(:)     ! 1-D ARRAY (ONE FOR EACH
                                                      ! RADIATION BEAM) OF 2-D GRID
                                                      ! STRUCTURES DEFINING BEAM
                                                      ! STRENGTH VS. CROSS-SECTION type (xray_point)  , allocatable :: point      (:)    ! LINEAR ENUMERATION OF ALL DATA
                                                      ! ASSOCIATED WITH EACH VOXEL USED
                                                      ! FOR THE OPTIMIZATION type (xray_boundary), allocatable :: boundary  (:)    ! POLYGON APPROXIMATING BOUNDARY
                                                      ! OF TISSUE-TYPE REGION IN A SLICE type (xray_center) , allocatable :: centers    (:)    ! LIST OF ALL ISO-CENTER LOCATIONS type (xray_tissues), allocatable :: tissues    (:)    ! TABLE OF INFORMATION ON ALL
                                                      ! DISTINCT TYPES OF TISSUES BEING
                                                      ! CONSIDERED
```

Appendix B - Source Code of Subroutines for Executing the Algorithm

```
***********************************************************************
        subroutine read_tissues (tissue_file)
        use xray character*(*)   ::  tissue_file call traceflow (1,'READ_TISSUES')

if (ldebug >= 3) write (*,*) 'TISSUE FILE = ',tissue_file open (3,file   = tissue_file,
     &        action  = 'READ',
     &        access  = 'SEQUENTIAL',
     &        status  = 'OLD',
     &        form    = 'FORMATTED')

if (ldebug >= 3) write (*,*) 'TISSUE FILE OPENED ' maxtypes = 5
+------------> do i=1,32768
|           read (3,*,end= 99,err= 99) itype,iclass,sigma
|           if (ldebug >= 3) write (*,'(1x,2i5,f10.4)') itype,iclass,sigma
|           maxtypes = max(itype,maxtypes)
+------------< end do 99 rewind (3)

if (ldebug >= 3) write (*,*) 'MAX TYPES   = ',maxtypes if (maxtypes <= 1) stop ' READ TISSUE TYPES' allocate (tissues(0:maxtypes))

!   ASSIGN DEFAULTS, ESPECIALLY AIR:
        tissues(0)%tclass= air   ;  tissues(0)%sigma = 1.0
        tissues(1)%tclass= bolus ;  tissues(1)%sigma = 1.0
        tissues(2)%tclass= norml ;  tissues(2)%sigma = 1.0
        tissues(3)%tclass= dense ;  tissues(3)%sigma = 1.0
        tissues(4)%tclass= tumor ;  tissues(4)%sigma = 1.0
        tissues(5)%tclass= avoid ;  tissues(5)%sigma = 1.0

+------------> do i=1,maxtypes
|           read (3,*,end=999,err=999) itype,iclass,sigma
|           tissues(itype)%tclass = iclass
|           tissues(itype)%sigma  = sigma
|           if (ldebug >= 3) write (*,'(1x,2i5,f10.4)') itype,iclass,sigma
+------------< end do 999 close (3)

call traceflow (2,'READ_TISSUES')

<======<<<  return
        end
```

```
**********************************************************************
        subroutine optimize (hist_tumor,hist_norml,hist_avoid,nh,
     &                       wt_n,wt_t,wt_a,wt_v)

use xray
        save real*4   :: hist_tumor(0:nh)
        real*4   :: hist_norml(0:nh)
        real*4   :: hist_avoid(0:nh)

integer*4 :: maxb_old = 0   ! used to tell if need
                                    ! to re-allocate matrices
*       ---------------------------------------------------------------
*       matrix data elements:
*       to solve:  A * c = b   ! sized to MAXB - NUMBER OF "ARCS"

!       THESE ARRAYS ARE ALLOCATED RATHER THAN AUTOMATIC
!       SINCE WE WANT TO BE ABLE TO RETAIN VALUES BETWEEN CALLS real*4, allocatable ::   a     (:)      ! system matrix
        real*4, allocatable ::   at    (:)      ! sub-matrix for specific tissue class
        real*4, allocatable ::   an    (:)      ! sub-matrix for specific tissue class
        real*4, allocatable ::   aa    (:)      ! sub-matrix for specific tissue class
        real*4, allocatable ::   vr    (:)      ! variance-reduction matrix
        real*4, allocatable ::   b     (:)      !
        real*4, allocatable ::   b0    (:)      !
        real*4, allocatable ::   bm_wt(:)
        real*4, allocatable ::   scale(:)       ! used to pre-scale beam weights in
                                                ! order to condition system matrix logical    :: reallocate         ! re-allocate system matrices ?
        logical    :: newfill            ! re-calculate system matrixes ?

logical    :: first = .true.     ! SET UP ATENUATION ARRAY call traceflow (1,'OPTIMIZE')

!       ---------------------------------------------------------------
!       INITIALIZE ATTENUATION FUNCTION
+------------> if (first) then
I               first = .false.
I               call setup_atten ()   ! FUNCTION OF BEAM ENERGY ?
+------------< end if
!       ---------------------------------------------------------------

C   DETERMINE CALCULATION OPTIONS:
            reallocate = (maxb_old .ne. maxb)
            maxb_old   = maxb +------------> if (reallocate) then
|+----------------> if ( allocated(a) ) then
||                      deallocate (a )      ! system matrix
||                      deallocate (at)      ! sub-matrix for specific tissue class
||                      deallocate (an)      ! sub-matrix for specific tissue class
||                      deallocate (aa)      ! sub-matrix for specific tissue class
||                      deallocate (vr)      ! variance-reduction matrix
||                      deallocate (b )      !
||                      deallocate (b0)      !
||                      deallocate (bm_wt)   ! vector to be solved for beam weights
||                      deallocate (scale)   ! used to pre-scale beam weights in
|+----------------< end if
|
|        C      ALLOCATE NEW STORAGE FOR MATRICES
|
|               allocate (a (maxb*maxb))     ! system matrix
|               allocate (at(maxb*maxb))     ! sub-matrix for specific tissue class
|               allocate (an(maxb*maxb))     ! sub-matrix for specific tissue class
|               allocate (aa(maxb*maxb))     ! sub-matrix for specific tissue class
|               allocate (vr(maxb*maxb))     ! variance-reduction matrix
|               allocate (b        (maxb))   !
```

2

```
|               allocate (b0       (maxb))   !
|               allocate (bm_wt    (maxb))   ! vector to be solved for beam weights
|               allocate (scale    (maxb))   ! used to pre-scale beam weights in
|                                            ! order to condition system matrix
+-------------< end if newfill   = newpoints .or. newbeams .or. newcenter
               newpoints = .false.
               newbeams  = .false.
               newcenter = .false.

!   re-set up beam base depths ?
+------------> if (newfill) then
|                  call make_beam_depth ()
+-------------< end if

*-------------------------------------------------------------
      *   fill up matrix elements:

+------------> if (newfill .or. reallocate) then
|                  call ax_fill (an,at,aa,vr,b0)
|
|      CXXX       call show_matrix (b0,maxb,    1,'VECTOR')
|      CXXX       call show_matrix (an,maxb,maxb,'NORMAL')
|      CXXX       call show_matrix (at,maxb,maxb,'TUMOR ')
|      CXXX       call show_matrix (aa,maxb,maxb,'AVOID ')
|      CXXX       call show_matrix (vr,maxb,maxb,'VR MATRIX')
|
|       !   Normalize matrixes to 1.000 as largest terms.
|       !   This removes some dependency on varying relative volumes when
|       !   combining by weights and does no real harm since AT is the
|       !   only matrix with a source term.
|
|                  atmax = maxval(at)         ! NOTE: abs(A) since A is positive definite
|+---------------> if (atmax > 0.00001) then
||                     at = at / atmax
||                     b0 = b0 / atmax
|+---------------< end if
|
|                  anmax = maxval(an)         ! NOTE: abs(A) since A is positive definite
|                  if (atmax > 0.00001) an = an / anmax
|
|                  aamax = maxval(aa)         ! NOTE: abs(A) since A is positive definite
|                  if (aamax > 0.00001) aa = aa / aamax
|
|                  vrmax = maxval(vr)         ! NOTE: abs(A) since A is positive definite
|                  if (vrmax > 0.00001) vr = vr / vrmax
+-------------< end if !   form weighted system matrix:
          a = wt_n*an + wt_t*at + wt_a*aa + wt_v*vr
          b =           wt_t*b0 call show_matrix (b ,maxb,    1,'VECTOR')
          call show_matrix (a ,maxb,maxb,'SYSTEM')

call show_matrix (an,maxb,maxb,'NORMAL')
          call show_matrix (at,maxb,maxb,'TUMOR ')
          call show_matrix (aa,maxb,maxb,'AVOID ')
          call show_matrix (vr,maxb,maxb,'VR MATRIX')

!   compute optimal beam weights:

call limiter (a,bm_wt,b,maxb)

!   RE-APPLY SCALE FACTORS THAT WERE TAKEN OUT TO CONDITION MATRIX
      !   TO BEAM WEIGHTS AND assign to beam structure:
+------------> do j=1,maxb
|+-----------> do jbeam = 1,numbeam
||+----------> if (beam(jbeam)%number == j) then
|||                beam(jbeam)%weight = bm_wt(j)
```

3

```
||+------------------< end if
|+----------------< end do
+--------------< end do

|      calculate resulting dosage & RE-NORMALIZE beam weights:
                call calc_dose ()

call dvhist (hist_tumor,nh,tumor)
                call dvhist (hist_norml,nh,norml)
                call dvhist (hist_avoid,nh,avoid)

call traceflow (2,'OPTIMIZE')

<=====<<<<      return
                end
```

```
***********************************************************
        subroutine make_points (ijskip)

C       WEIGHT POINTS ON BOTTOM SLICE MORE TO ACCOUNT FOR UN-IMAGED TISSUE ???
C       (I.E. VOLUME -> VOLUME * N  ???)

use xray integer         :: ttype,tissue integer*2       :: vox
        logical         :: only_counting
        logical         :: jat,kat
        logical         :: dense_type,not_skip

*       ----------------------------------------------------
!       determine "best" Z decimation factor as a function
!       of slice thickness and horizontal skip factor:

call traceflow (1,'MAKE_POINTS')

newpoints = .true.

kskip = nint(float(ijskip)* sqrt(xthick*ythick)/ zthick )
        kskip = max(kskip,1)

only_counting = .true.

volume_dense = xthick * ythick * zthick
        volume_skip  = volume_dense * float(kskip * ijskip**2)

10     continue   ! restart here after count points numpt = 0
        do k=klo,khi
           kat = modulo(k-klo,kskip) == 0
           do j=jlo,jhi
              jat = modulo(j-jlo,ijskip) == 0
              do i=ilo,ihi
                 vox   = voxel(i,j,k)
                 tissue = abs(vox)
                 ttype = tissues(tissue)%tclass
                             ! CATEGORIZE ALL TISSUE AS
                             ! AIR,BOLUS,NORML,DENSE,AVOID,TUMOR
                 if ((ttype == air    .or.
     &                ttype == bolus     ) cycle dense_type = ttype == tumor .or.
     &                        ttype == avoid .or.
     &                        ttype == dense .or.
     &                        vox < 0              ! NEAR TUMOR not_skip = kat .and. jat .and. modulo(i-ilo,ijskip)==0 if (dense_type .or. not_skip) then
                    numpt = numpt + 1
                    if (only_counting) cycle
                    point(numpt)%x     = float(i-ilo) * xthick + xlo
                    point(numpt)%y     = float(j-jlo) * ythick + ylo
                    point(numpt)%z     = float(k-klo) * zthick + zlo
                    point(numpt)%index = vox
                    point(numpt)%tclass = ttype
                    point(numpt)%sigma = tissues(tissue)%sigma   !C##### SIGMA HERE
                    if (dense_type) then
                       point(numpt)%volume = volume_dense
                    else
                       point(numpt)%volume = volume_skip
                    end if
                 end if
              end do
           end do
```

5

```
+-------------< end do num_pts = numpt

+-------------> if (only_counting) then    ! ALLOCATE ARRAY & POPULATE IT
I                 only_counting = .false.
I                 if (allocated(point)) deallocate (point)
I                 allocate (point(num_pts))
<=====<<<<        go to 10
+-------------< end if call show_points ()

call traceflow (2,'MAKE_POINTS')

<=====<<<<    return
              end
```

```
******************************************************************
        subroutine make_boundary ()
        use xray logical        :: only_counting

*       ---------------------------------------------------------
        call traceflow (1,'MAKE_BOUNDARY')

only_counting = .true.

10 continue   ! RESTART HERE AFTER ALLOCATE ARRAY TO POPULATE IT
        numpt = 0

+-------------> do k=klo+1,khi-1
|                 km = k-1
|                 kp = k+1
|+------------> do j=jlo+1,jhi-1
||                jm = j-1
||                jp = j+1
||+-----------> do i=ilo+1,ihi-1
|||               if (voxel(i,j,k) == 0 ) cycle

|||               im = i-1
|||               ip = i+1

|||               if (voxel(im,j ,k ) == 0 .or.
|||     &             voxel(ip,j ,k ) == 0 .or.
|||     &             voxel(i ,jm,k ) == 0 .or.
|||     &             voxel(i ,jp,k ) == 0 .or.
|||     &             voxel(i ,j ,km) == 0 .or.
|||+----------> &   voxel(i ,j ,kp) == 0 ) then   ! ON AN EDGE OF "AIR"
||||
||||              numpt = numpt + 1
||||
||||              if (only_counting) cycle
||||              boundary(numpt)%x = float(i-ilo) * xthick + xlo
||||              boundary(numpt)%y = float(j-jlo) * ythick + ylo
||||              boundary(numpt)%z = float(k-klo) * zthick + zlo
|||+----------< end if
||+------------< end do
|+-------------< end do
+--------------< end do C    ADD IN ALL NON-ZERO POINTS IN FIRST AND LAST SLICES:
+-------------> do k=klo,khi,(khi-klo)  ! only does klo & khi
|+------------> do j=jlo+1,jhi-1
||+-----------> do i=ilo+1,ihi-1
|||               if (voxel(i,j,k) ==0 ) cycle
|||               numpt = numpt + 1
|||               if (only_counting) cycle
|||               boundary(numpt)%x = float(i-ilo) * xthick + xlo
|||               boundary(numpt)%y = float(j-jlo) * ythick + ylo
|||               boundary(numpt)%z = float(k-klo) * zthick + zlo
||+------------< end do
|+-------------< end do
+--------------< end do numboundary = numpt +-------------> if (only_counting) then   ! ALLOCATE ARRAY & POPULATE IT
|                 only_counting = .false.
|                 if (allocated(boundary)) deallocate (boundary)
|                 if (ldebug >= 3) write (*,*) "number boundary =",numboundary
|                 allocate (boundary(numboundary))
<======<<<<       go to 10
+--------------< end if call traceflow (2,'MAKE_BOUNDARY')
<======<<<<  return
        end
```

```
***************************************************
        subroutine dose_out (dose_file,d)
        use xray character*(*)  :: dose_file
        character      :: d(ilo:ihi,jlo:jhi,klo:khi)

call traceflow (1,'DOSE_OUT')

open (4,file   = dose_file,
     &        action  = 'WRITE',
     &        access  = 'SEQUENTIAL',
     &        status  = 'UNKNOWN',
     &        form    = 'UNFORMATTED')

numx = ihi - ilo + 1
        numy = jhi - jlo + 1
        numz = khi - klo + 1 write (4)  numx,xlo,xthick, numy,ylo,ythick, numz,zlo,zthick
        write (4) d
        close (4)

call traceflow (2,'DOSE_OUT')

<=====<<<<    return
        end
```

```
***************************************************************
      subroutine read_voxel (voxelfile)
      use xray character*(*)   voxelfile call traceflow (1,'READ_VOXEL')

inputfile = voxelfile open (4,file   = voxelfile,
     &      action   = 'READ',
     &      access   = 'SEQUENTIAL',
     &      status   = 'OLD',
     &      form     = 'UNFORMATTED')

if (allocated(voxel)) deallocate (voxel)

CXXX  read  (4)  ilo,ihi, jlo,jhi, klo,khi, ithick
      read  (4)  numx,xlo,xthick, numy,ylo,ythick, numz,zlo,zthick ilo = 1
      jlo = 1
      klo = 1
      ihi = numx
      jhi = numy
      khi = numz allocate (voxel( ilo:ihi , jlo:jhi , klo:khi ))

if (ldebug >= 3) write (*,"(a,f6.2,a)") " voxel array =",
     & 2.0 * float((ihi-ilo+1)*(jhi-jlo+1)*(khi-klo+1))/1024.0**2,
     & " mbytes"

read  (4)  voxel
      close (4)
!     ---------------------------------------- newpoints = .true.

call traceflow (2,'READ_VOXEL')

<=====<<<<    return
      end
```

```
***************************************************************
        subroutine make_beams (mintab,maxtab,movtab,
     &                         mingan,maxgan,movgan,
     &                         conesize, lock)
        use xray
        save integer*4 mintab,maxtab,movtab
        integer*4 mingan,maxgan,movgan logical   lock          ! controls whether all "beams" in
                                ! one arc are considered together real*4    conesize
                ! CONESIZE [ <=0] ===> SILHOUETTE
                ! CONESIZE [0..2] ===> AUTOMATIC CONE SIZE
                ! CONESIZE [ >=2] ===> ACTUAL MM SIZE

*       ----------------------------------------------------- call traceflow (1,'MAKE_BEAMS')

newbeams = .true.               ! GLOBAL if (allocated(beam)) deallocate (beam)

numbeam = 0
+------------> do j=mintab,maxtab,movtab
|+-----------> do i=mingan,maxgan,movgan
||                numbeam = numbeam + numiso   ! NOTE: # ISOCENTERS !!!
|+-----------< end do
+------------< end do numcollim = 1

!       one extra [false] beam to stop lock process on last arc
        allocate (beam       (1:numbeam+1))
        allocate (beam_shape(1:numbeam  ))
        allocate (beam_depth(1:numbeam  ))
*       -----------------------------------
*       set up beam structure information:

n      = 0    ! CUMULATIVE INDEX IN BEAM ARRAY
        number = 0    ! BEAM/ARC NUMBER C   COLIMATOR ANGLE TO BE IMPLEMENTED LATER, IF NECESSARY:
        collim = 0.0
        cc = cos(collim*d2r)
        sc = sin(collim*d2r)

+------------> do iso=1,numiso
|               x00   = centers(iso)%x0
|               y00   = centers(iso)%y0
|               z00   = centers(iso)%z0
|               cone00= centers(iso)%radius_max
|
|+-----------> do itable = mintab,maxtab,movtab
||               table = float(itable)
||               ct    = cos(table*d2r)
||               st    = sin(table*d2r)
||
||   *          make gantry angle the inner-most loop.
||   *          this allows easy locking/unlocking the arc components
||   *          and ensures that all locked components occur together
||   *          in the structure array.
||
||               if (lock) number = number+1
||
||+----------> do igantry=mingan,maxgan,movgan
|||               if (.not.lock) number = number + 1
```

```
                        gantry = float(igantry)
                        cg     = cos(gantry*d2r)
                        sg     = sin(gantry*d2r)

n= n + 1 beam(n)%number      = number
                        beam(n)%isocenter   = iso beam(n)%x0          = x00
                        beam(n)%y0          = y00
                        beam(n)%z0          = z00
                        beam(n)%radius_max  = cone00
                        beam(n)%conesize    = conesize beam(n)%table_angle   = table
                        beam(n)%gantry_angle  = gantry
                        beam(n)%collim_angle  = collim beam(n)%a = (sc*st-cc*cg*ct)
                        beam(n)%b = (cc*sg          )
                        beam(n)%c = (cc*cg*st+sc*ct)

beam(n)%d = (cc*st-sc*cg*ct)
                        beam(n)%e = (sc*sg          )
                        beam(n)%f = (sc*cg*st+cc*ct)

beam(n)%g = (sg*ct          )
                        beam(n)%h = (cg             )
                        beam(n)%i = -(sg*st         )

|+---------------< end do         ! GANTRY ANGLE
|+---------------< end do         ! ARC / TABLE ANGLE
+-------------< end do            ! ISO-CENTER beam(n+1)%number = number + 1  ! mark change of beam number
                                               ! on EXTRA beam maxb = number  ! max beam number = # arcs = degrees of freedom +-------------> if (conesize >= 0.0) then
I                       call cone_shape ()
I                       ! MAKE CONESIZE(BEAM) A FUNCTION OF
I                       ! BEAM'S EYE/ARC'S EYE VIEW MAX_RADIUS ?
+--------------= else
I                       call silhouette ()
I                       ! "POINT" HAS A DENSE SAMPLING OF ALL TUMOR VOXELS
I                       ! MAKE SILHOUETTE ONLY KEY ON MATCHING ISO-CENTER POINTS ?
+-------------< end if call traceflow (2,'MAKE_BEAMS')

<=====<<<<      return
                end
```

```
            subroutine make_beam_depth ()
*      set up the beam base depth of all beams

*      FOR EACH SLICE, ADD POINTS AT SAME X,Y BUT AT
*      INTERMEDIATE THICKNESSES TO ENSURE DENSE FILL ?

use xray

!           LEAVE BORDER FOR INTERPOLATION:
            integer*4, parameter :: mmax = (max_grid + 4)
            real*4           :: work(-mmax:mmax,-mmax:mmax)
            logical*1        :: flag(-mmax:mmax,-mmax:mmax)

type (xray_beam) :: temp call traceflow (1,'MAKE_BEAM_DEPTH')

call make_boundary ()  ! FILL UP BOUNDARY POINT STRUCTURE,
                                   ! DEALLOCATE WHEN DONE UNLESS WANT PLOTS
*-------------------------------------------------
            nn = max_grid-1
            do j=1,numbeam
               temp = beam(j)

x00 = temp%x0
               y00 = temp%y0
               z00 = temp%z0

*              INIT BEAM DEPTH:
               work = 0.0
               flag = .true.

if (ldebug >= 3) write (*,"(1x,a,i5,a )") "beam:", j," "

do i=1,numboundary
*                 ADD ANOTHER INNER LOOP TO SPAN THICKNESS FROM 0 TO N-1 ?
*                 find coordinates relative to iso-center
                  x1 = boundary(i)%x - x00
                  y1 = boundary(i)%y - y00
                  z1 = boundary(i)%z - z00

*                 project to beam cordinates
                  x2 = temp%a*x1 + temp%b*y1 + temp%c*z1
                  y2 = temp%d*x1 + temp%e*y1 + temp%f*z1
                  z2 = temp%g*x1 + temp%h*y1 + temp%i*z1 if (z2 < 0.0) cycle      ! DON'T WANT BACK-SIDE OF HEAD

*                 correct lateral coordinates for beam spread:
                  factor = (arc_radius-z2) / arc_radius  !C### VERIFY SIGN !!!
                  i2 = nint(x2 / factor)
                  j2 = nint(y2 / factor)

CXXX              WRITE (*,"(' DEPTH',3I5, F8.2)") J,I2,J2,Z2 if (iabs(i2) <= mmax .and.
     &                iabs(j2) <= mmax ) then

CXXX                 WRITE (*,"(' DEPTH',3I5,2F8.2)")
CXXX &                  J,I2,J2,Z2,WORK(I2,J2)  !C###???!!

work(i2,j2) = max(z2,work(i2,j2))
                     flag(i2,j2) = .false.
                  end if
               end do call sordata (work,flag,mmax,0.1)

beam_depth(j)%grid = work(-max_grid:max_grid,
```

```
|              &                        -max_grid:max_grid) ! ARRAY SECTION
|              call show_beam_depth (beam_depth(j)%grid,max_grid,j)
+-------------< end do deallocate (boundary)    ! RETAIN FOR DEBUG PLOTS ?

call traceflow (2,'MAKE_BEAM_DEPTH')

<=====<<<      return
               end
```

```
***************************************************
        subroutine sordata (z,flag,mm,epsilon)

use xray, only: ldebug c       Simultaneous Over Relaxation solution to Laplace's equation
c       using Chebyshev acceleration (p. 659 of "Numerical Recipies")

parameter (w       = 1.5)
        parameter (maxiter = 500)
        parameter (miniter =  10)

real*4    z    (-mm:mm,-mm:mm)
        logical*1 flag(-mm:mm,-mm:mm)

*       ---------------------------------
        nn = mm

CXXX    write (*,*) ' SOR:'
CXXX    write (*,*) ' Iter Error Err/Epsilon '
CXXX    write (*,*) ' ' i1 = -mm    ! SET INTERPOLATION LIMITS TO WHOLE ARRAY !!!
        m  =  mm    ! SET INTERPOLATION LIMITS TO WHOLE ARRAY !!!
        j1 = -nn    ! SET INTERPOLATION LIMITS TO WHOLE ARRAY !!!
        n  =  nn    ! SET INTERPOLATION LIMITS TO WHOLE ARRAY !!!

i2 = i1+1
        j2 = j1+1 m1 = m-1
        n1 = n-1

+-------------> do 900 iter=1,maxiter rmax = 0.0           ! save maximum residual so that we can know
                               ! when we are done call show_sordata (z,flag,mm,iter)  !C### c         do center of 2-d array (i.e. not the edges or corners)
+-------------> do 200 j=j2,n1
                  jp = j+1
                  jm = j-1
                  i0 = modulo(j+iter,2) + j2    ! either start at 2 or 3
+-----------------> do 100 i=i0,m1,2            ! and do every other point
+---------------------> if (flag(i,j)) then
|                         resid =(z(i,jp)+z(i,jm)+z(i+1,j)+z(i-1,j))/4.0-z(i,j)
|                         rmax  = max(rmax,abs(resid))
|                         z(i,j)= z(i,j) + w*resid
+---------------------< end if
+-------< 100       continue
+-------< 200   continue c       ---------------------------------------------
        c       do four edges of 2-d array:
                j = j1
                j2= j2
+---------------> do 300 i=i2,m1
+-----------------> if (flag(i,j)) then
|                     resid = (z(i,j2)+z(i+1,j)+z(i-1,j))/3.0 - z(i,j)
|                     rmax  = max(rmax,abs(resid))
|                     z(i,j)= z(i,j) + w*resid
+-----------------< end if
+-------< 300   continue j = n
                jm= n-1
+---------------> do 400 i=i2,m1
+-----------------> if (flag(i,j)) then
|                     resid = (z(i,jm)+z(i+1,j)+z(i-1,j))/3.0 - z(i,j)
```

```
||              rmax  = max(rmax,abs(resid))
||              z(i,j)= z(i,j) + w*resid
|+----------------< end if
+--------< 400   continue i = i1
                i2= i2
+----------------> do 500 j=j2,n1
|+---------------> if (flag(i,j)) then
||                  resid = (z(i,j+1)+z(i,j-1)+z(i2,j))/3.0 - z(i,j)
||                  rmax  = max(rmax,abs(resid))
||                  z(i,j)= z(i,j) + w*resid
|+----------------< end if
+--------< 500   continue i = n
                im= n-1
+----------------> do 600 j=j2,n1
|+---------------> if (flag(i,j)) then
||                  resid = (z(i,j+1)+z(i,j-1)+z(im,j))/3.0 - z(i,j)
||                  rmax  = max(rmax,abs(resid))
||                  z(i,j)= z(i,j) + w*resid
|+----------------< end if
+--------< 600   continue c       ---------------------------------------------
        c       do four corners:
+---------------> if (flag(m,n)) then
|                   resid = (z(m,n-1)+z(m-1,n))/2.0 - z(m,n)
|                   rmax  = max(rmax,abs(resid))
|                   z(m,n)= z(m,n) + w*resid
+---------------< end if +---------------> if (flag(i1,n)) then
|                   resid = (z(i1,n-1)+z(i2,n))/2.0 - z(i1,n)
|                   rmax  = max(rmax,abs(resid))
|                   z(i1,n)= z(i1,n) + w*resid
+---------------< end if +---------------> if (flag(m,j1)) then
|                   resid = (z(m,j2)+z(m-1,j1))/2.0 - z(m,j1)
|                   rmax  = max(rmax,abs(resid))
|                   z(m,j1)= z(m,j1) + w*resid
+---------------< end if +---------------> if (flag(i1,j1)) then
|                   resid = (z(i1,j2)+z(i2,j1))/2.0 - z(i1,j1)
|                   rmax  = max(rmax,abs(resid))
|                   z(i1,j1)= z(i1,j1) + w*resid
+---------------< end if
        c       ---------------------------------------------
        CXXX    write (*,'(a,i5,f8.4,f8.1)') ' ',iter,rmax,rmax/epsilon +---------------> if (rmax .lt. epsilon .and. iter.ge.miniter) then   ! DONE ?
|                   if (ldebug >= 3) write (*,'(20x,a,i5,a,f8.4)')
|       ?                               ' Iter:',iter," residual:",rmax
<=====<<<<          return
|+---------------< end if
+--------< 900   continue c       if fall through loop # 900, then did not converge within expected
        c       number of iterations:

CXXX    write (*,'(a,i5,f8.4,f8.1)')
        CXXX >  ' **** Maximum # iterations exceeded in SORDATA ****',
        CXXX >     iter,rmax,rmax/epsilon <=====<<<<      return
                end
```

```
***************************************************************
        subroutine silhouette ()

C####   NEED TO REGULARIZE & INTERPOLATE TO FILL IN GAPS IN
C####   SLICES, ESPECIALLY SINCE WITH ANGLES = 0,0 SLICES MAP
C####   TO DISJOINT HORIZONTAL LINES
*       ---------------------------------------------------------
*       define the beam shape component of all beams as silhouette of tumor use xray call traceflow (1,'SILHOUETTE')

call cone_shape ()   !CXXX  TEMPORARY FIX call traceflow (2,'SILHOUETTE')

<=====<<<<  return
        end
```

```
***********************************************************
        subroutine ax_fill (an,at,aa,vr,b)
        use xray real*4    at(maxb,maxb)   ! tumor
        real*4    an(maxb,maxb)   ! normal tissue
        real*4    aa(maxb,maxb)   ! avoidance areas
        real*4    vr(maxb,maxb)   ! variance reduction
        real*4    b (maxb)

CXXX    NOTE THE +1 !!!
CXXX    type (xray_beam)     :: beam       (numbeam+1)

CXXX    character*8 ctotal    !C#### analysis of total # cross terms

*       -----------------------------------------
*       local storage:

parameter (beam_min = 0.0001)    ! dose < this assumed to be == 0 real*4    dk(maxb)      ! dosage for beam(kk(_)) at point(x,y,z)
        integer*4 kk(maxb)      ! beam number for dose dk(_)

CXXX    real*4    hist_non(0:maxb) = 0.0 ! plot for analysis
CXXX    real*4    hist_val(0:maxb) = (/(float(i),i=0,maxb /)

integer*4 pt_type
        real*4    pt_volume call traceflow (1,'AX_FILL')

!       -----------------------------------------------------------
*       initialize arrays:
        b  = 0.0
        at = 0.0
        an = 0.0
        aa = 0.0

*       -----------------------------------------------------------
*       for each point:

non_total= 0       ! total number of cross terms
+------> do ipt=1,num_pts
|          pt_type = point(ipt)%tclass
|          if (pt_type == bolus) cycle
|
|          pt_volume =     point(ipt)%volume
|          pt_weight = 1.0/point(ipt)%sigma          !C###### SIGMA HERE
|
|     *    calculate dose at this point for each beam:
|
|          non_zero = 0       ! number of non-'zero' beams for this point
|          dose     = 0.0     ! accumulator for possible arc dosage
|
+------>   do jbeam=1,numbeam
|            k = beam(jbeam)%number
|
|       *   find coordinates relative to iso-center
|           x1 = point(ipt)%x - beam(jbeam)%x0
|           y1 = point(ipt)%y - beam(jbeam)%y0
|           z1 = point(ipt)%z - beam(jbeam)%z0
|
|       *   project to beam coordinates
|           x2 = beam(jbeam)%a*x1 + beam(jbeam)%b*y1 + beam(jbeam)%c*z1
|           y2 = beam(jbeam)%d*x1 + beam(jbeam)%e*y1 + beam(jbeam)%f*z1
|           z2 = beam(jbeam)%g*x1 + beam(jbeam)%h*y1 + beam(jbeam)%i*z1
|
|       *   correct lateral coordinates for beam spread:
|           factor = (arc_radius-z2) / arc_radius  !C### VERIFY SIGN !!!
|           i2 = nint(x2 / factor)
```

```
                      j2 = nint(y2 / factor)
                      if (abs(i2) <= max_grid .and.
+---------> &             abs(j2) <= max_grid) then
|
|                         nindex = nint(beam_depth(jbeam)%grid(i2,j2)-z2 )
|
|+------------------> if (nindex < min_atten) then
||     CXXX              write (*,*) ' *** ATTEN INDEX =',nindex
||                       nindex = min_atten
|+---------------------= else
||                       nindex = min(nindex,max_atten)
|+--------------------< end if
|
|                         dose = dose + beam_shape(jbeam)%grid(i2,j2) *
|           &             atten(nindex) / factor**2 ! spherical spreading
|
+----------------< end if +----------------> if (k /= beam(jbeam+1)%number) then
|       |             move to new distinct beam/fan/arc
|                     ddose = dose  ! save temporary value
|                     dose  = 0.0   ! re-initialize
|
|+-------------------> if (ddose >= beam_min) then
||                        non_zero = non_zero + 1
||                        non_total= non_total+ 1
||
||                        kk(non_zero) = k         ! remember actual beam number
||
||                        dk(non_zero) = ddose * pt_volume * pt_weight
||
||                                            ! multiply by volume * weight only once
||
||                        select case (pt_type)  !C### VERIFY ONLY DOES ONE BLOCK
||                        case (tumor)
||                           b(k) = b(k) + ddose
||+---------------------> do j=1,non_zero           ! lower half only
|||                          at(k,kk(j))=at(k,kk(j))+ddose*dk(j)
||+---------------------< end do
||                        case (norml,dense)
||+---------------------> do j=1,non_zero           ! lower half only
|||                          an(k,kk(j))=an(k,kk(j))+ddose*dk(j)
||+---------------------< end do
||                        case (avoid)
||+---------------------> do j=1,non_zero           ! lower half only
|||                          aa(k,kk(j))=aa(k,kk(j))+ddose*dk(j)
||+---------------------< end do
||                        case default
||                           write (*,*) '*** UNKNOWN TYPE - BUG ALERT ***'
<======<<<<               go to 99  ! go to new point
 ||                       end select
 ||
 |+---------------------< end if
 +------------------< end if            ! end on test for new beam
 +---------------< end do               ! end loop on beams
        99        continue              ! next point
        CXXX      hist_non(non_zero) = hist_non(non_zero) + 1.0
+---------------< end do                ! end loop on points

*     ---------------------------------
         *     Matrix built:

*     fill in symmetric part:

+--------------> do k=1,maxb
|                  vr(k,k) = at(k,k) + an(k,k) + aa(k,k)
|+-------------> do l=1,k-1
||                 at(l,k) = at(k,l)
||                 an(l,k) = an(k,l)
||                 aa(l,k) = aa(k,l)
```

```
                        vr(k,l) = at(k,l) + an(k,l) + aa(k,l)
                        vr(l,k) = vr(k,l)
|+---------------< end do
+---------------< end do
            call vr_form (vr,maxb)      ! make optional Variance Reduction matrix if (ldebug >= 3)
          & write (*,'(a,i9)') ' Number of non-zero partials = ',non_total CXXX  write (ctotal,'(i8)') non_total              !C#### analysis
    CXXX  call xyplot (hist_val(0),hist_non(0),        !C#### analysis
    CXXX &    maxb+1,                                  !C#### analysis
    CXXX &  '# non-zero terms','# occurrences',        !C#### analysis
    CXXX &  'non-zero histogram: total ='//ctotal,     !C#### analysis
    CXXX &   10.0,5.0)                                 !C#### analysis call traceflow (2,'AX_FILL')

<======<<<<   return
              end
```

```
****************************************************
          subroutine vr_form (v,n)

parameter (vr_epsilon = 0.0001)

*    add terms to system matrix that will tend to
     *    reduce the LOCAL variance of the resulting solution vector
     *    this should also tend to make the convergence both
     *    more stable and more rapid.

*    input:  v = total dot product matrix (non-normalized)
     *    output: v = variance reduction matrix real*4 v(n,n)

real*4 :: c(n)  ! FORTRAN 90 VARIABLE STORAGE call traceflow (1,'VR_FORM')

*    ---------------------------------------------------------
     *    NORMALIZE TO MAKE DIAGONALS == 1.000

+--------------> do i=1,n
|                  vii  = max( v(i,i) , 0.0001)   !CXXX ??? !!! WHY ERROR HERE ?
|                  c(i) = 1.0/sqrt(vii)
+--------------< end do +--------------> do j=1,n
|+--------------> do i=1,n
||                 v(i,j) = v(i,j) * (c(i)*c(j))
|+--------------< end do
+--------------< end do C#### call matprint (v,n,'Cross-Correlation Matrix <====<<<')

*    WE NOW HAVE A NORMALIZED "CROSS-CORRELATION" MATRIX
     *    OF BEAM SIGNATURES

*    MAKE ALL ROWS AND COLUMNS ADD UP TO ZERO, WITH ONES ON THE DIAGONAL
     *    AND OFF-DIAGONAL TERMS PROPORTIONAL TO THE DOT PRODUCT

+--------------> do j=1,n
|                  v(j,j) = 0.0              ! take out diagonal, put back later
+--------------< end do

*    SOLVE FOR SCALE FACTORS THAT WILL MAKE ROW & COLUMN SUMS == +1

+--------------> do iter=1,100
|       *         BY LINE ONLY (REMEMBER MATRIX IS SYMMETRIC & WILL REMAIN SO):
|                  del = 0.0
|+--------------> do j=1,n
||                 sum = 0.0
||+--------------> do i=1,n
|||                  sum = sum + v(i,j)
||+--------------< end do
||+--------------> do i=1,n
|||+--------------> if (abs(sum) > 0.0001) then   ! safe on divide by zero
||||                 vij = v(i,j) / sum
||||                 del = max(del,abs(vij-v(i,j)))
|||+--------------= else
||||                 vij = 0.0
|||+--------------< end if

||                   v(i,j) = vij
||                   v(j,i) = vij       ! FILL IN SYMMETRIC PART (COLUMN)
||+--------------< end do
|+--------------< end do
|        CXXX      write (*,'(1x,i6,f10.5)') iter,del
<====<<<           if (del < vr_epsilon) go to 999
+--------------< end do  ! ON ITER
```

20

```
          999 continue
      *       PUT V BACK IN NECESSARY FORM, WITH "1" ON DIAGONAL,
      *       AND COLUMNS & ROWS ADDING UP TO ZERO:

+-------------> do j=1,n
|+--------------> do i=1,n
||                   v(i,j) = -v(i,j)    !C#### POSSIBLY USE  -SQRT INSTEAD ?
|+--------------< end do
|                 v(j,j) = 1.0
+-------------< end do C#### call matprint (v,n,'Variance Reduction Matrix <====*<<<')

call traceflow (2,'VR_FORM')

<=====<<<<    return
              end
```

```
***************************************************************
        subroutine calc_dose ()

use xray call traceflow (1,'CALC_DOSE')

*       ----------------------------------------------------------------
        sum2tumor = 0.0
        sum_tumor = 0.0       ! find average tumor dose & re-scale
        vol_tumor = 0.0       !    to full desired dose:

*       for each point:
+-------> do ipt=1,num_pts

C####   if (point(ipt)%tclass == BOLUS) then    !C#### need dose in BOLUS
        C####       point(ipt)%dose = 0.0              !C#### for plots
        C####       cycle
        C####   end if dose = 0.0

+-------> do jbeam=1,numbeam

*       find coordinates relative to iso-center
                x1 = point(ipt)%x - beam(jbeam)%x0
                y1 = point(ipt)%y - beam(jbeam)%y0
                z1 = point(ipt)%z - beam(jbeam)%z0

*       project to beam coordinates
                x2 = beam(jbeam)%a*x1 + beam(jbeam)%b*y1 + beam(jbeam)%c*z1
                y2 = beam(jbeam)%d*x1 + beam(jbeam)%e*y1 + beam(jbeam)%f*z1
                z2 = beam(jbeam)%g*x1 + beam(jbeam)%h*y1 + beam(jbeam)%i*z1

*       correct lateral coordinates for beam spread:
                factor = (arc_radius-z2) / arc_radius  !C### VERIFY SIGN !!!
                i2 = nint(x2 / factor)
                j2 = nint(y2 / factor)
+-------> if (abs(i2) <= max_grid .and. abs(j2) <= max_grid) then C#####  MAKE SURE COUNTING MULTIPLE BEAMS CORRECTLY
        C#####  ESPECIALLY IF DIFFERENT ARCS HAVE DIFFERENT # OF COMPONENTS nindex = nint(beam_depth(jbeam)%grid(i2,j2)-z2 )

! PUT DEBUG CHECK IN FUNCTION ATTEN (?)

+-------> if (nindex < min_atten) then
||  CXXX        write (*,*) ' *** ATTEN INDEX =',nindex
||              nindex = min_atten
+-------= else
||              nindex = min(nindex,max_atten)
+-------< end if dose = dose + beam(jbeam)%weight       *
        &                   beam_shape(jbeam)%grid(i2,j2) *
        &           atten(nindex) / factor**2 ! spherical spreading +-------< end if
                ! PRE-MULTIPLY WEIGHT BY BEAM SHAPE TO SAVE TIME & RECOVER LATER?
+-------< end do
                point(ipt)%dose = dose

*       ACCUMULATE DOSAGE STATISTICS ON TUMOR VOLUME:
+-------> if (point(ipt)%tclass == tumor) then
                sum_tumor = sum_tumor + point(ipt)%volume * dose
                sum2tumor = sum2tumor + point(ipt)%volume * dose**2
                vol_tumor = vol_tumor + point(ipt)%volume
+-------< end if
+-------< end do
```

```
+-------------> if (vol_tumor <= 0.000) then
|                   write (*,*)'**** NO TUMOR TYPE POINTS FOUND IN CALC_DOSE ****'
|                   stop
+-------------< end if avg_tumor = sum_tumor/vol_tumor
                sig_tumor = sqrt(sum2tumor/vol_tumor - avg_tumor**2) !C###  UNITS ???

*       re-scale to force desired dose in tumor:
        *       this is equivalent to optimizing with a larger prescription:
                re_scale = 1.0 / avg_tumor

*       re-normalize beam weights:
+-------------> do jbeam = 1,numbeam
|                   beam(jbeam)%weight = beam(jbeam)%weight * re_scale
+-------------< end do +-------------> do ipt =1,num_pts
|                   point(ipt)%dose = point(ipt)%dose * re_scale
+-------------< end do avg_tumor = avg_tumor * re_scale
                sig_tumor = sig_tumor * re_scale call traceflow (2,'CALC_DOSE')

<=====<<<<      return
                end
```

```
***************************************************
        real*4 function atten (i)
        use xray i = max(i,min_atten)
        i = min(i,max_atten)

num_atten(i) = num_atten(i) + 1
        atten = tab_atten(i)

<=====<<<<      return
        end
```

```
*************************************************************
          subroutine setup_atten ()

use xray

*         ----------------------------------------------------------------
*         dosage model parameters:

parameter (depth_max_dose = 30.0 ) ! depth of dosage maximum (mm)
          parameter (b0=8.60)                ! secondary attenuation depth (mm)

call traceflow (1,'SETUP_ATTEN')

C      a0 is primary attenuation depth
          a0 = b0*(exp(depth_max_dose/b0)-1.0)

C      scale factor to make ==1 @ xmax
          c0 = 1.0/(b0 * exp(-depth_max_dose/a0) *
       &       (1.0-exp(-depth_max_dose/b0)) )

+------------> do i=0,max_atten
|                 depth = float(i)          !C####   TIMES SCALE_FACTOR TO BE DEFINED
|                 tab_atten(i) = c0*b0*exp(-depth/a0)*(1.0-exp(-depth/b0))
+------------< end do tab_atten(:-1) = tab_atten(0) ! ALLOW FOR "NEGATIVE" VALUES num_atten = 0    ! INITIALIZE ATTENUATION HISTOGRAM call traceflow (2,'SETUP_ATTEN')

<=====<<<   return
          end
```

```
************************************************************
        subroutine liniter (a,x,b,n)
        use xray, only: ldebug

*    +---------------------------------------------------------------+
*    | Iteratively solve A*X=B as on p. 301-306 of                   |
*    |    "Modern Mathematical Analysis" by Protter & Morrey,        |
*    |    Addison-Wesley (1964)                                      |
*    +---------------------------------------------------------------+
*    | The matrix A must be "dominately" diagonal. A re-arrangement  |
*    | of terms and a re-scaling is done here to force diagonal      |
*    | terms to have the value of 1.0 . This accomplishes diagonal   |
*    | dominance and saves dividing by the diagonal terms many       |
*    | times during the solution.                                    |
*    +---------------------------------------------------------------+
*    +---------------------------------------------------------------+
*    | The actual number of iterations required will depend upon the |
*    | structure of the matrix (on how many elements approach the    |
*    | diagonal terms in value.                                      |
*    +---------------------------------------------------------------+
*    | This version constrains all elements of the solution vector   |
*    | to be >= 0.0                                                  |
*    +---------------------------------------------------------------+ implicit real*4 (a-h,o-z)

real*4              :: a  (n,n)
        real*4              :: x  (n)
        real*4              :: b  (n)
        real*4              :: scale(n)  ! automatic array real*4   , parameter :: epsilon = 0.0001
        real*4   , parameter :: omega_l = 0.65
        integer*4, parameter :: maxiter = 2000 call traceflow (1,'LINITER')

*       ----------------------------------------------------
*       normalize to make diagonals == 1.000
+--------------> do i=1,n
|                  scale(i) = 1.0/sqrt(a(i,i))
+--------------< end do +--------------> do j=1,n
|                  b(j) = b(j) * scale(j)
|  +-----------> do i=1,n
|  |                a(i,j) = a(i,j) * (scale(i)*scale(j))
|  +-----------< end do
+--------------< end do
*       ---------------------------------------------------- numj = min(8,n)
        if (ldebug >= 3) write (*,*) 'Solving for Beam Weights:'
        if (ldebug >= 3) write (*,'(a,8i8)') '  Iter     error',(j,j=1,numj)

+--------------> do i=1,n
|                  x(i) = 0.0
+--------------< end do

+--------------> do iter = 1,maxiter
|                  dimax = 0.0
|                  xmax  = 0.0
|  +-----------> do j=1,n
|  |                xtem = b(j)
|  |  +--------> do i=1,n
|  |  |             xtem = xtem - a(i,j)*x(i)    ! NOTE: CHECK INDEX ORDER
|  |  +--------< end do
|  |            C##########xtem = x(j) + omega_l*xtem/a(j,j)  ! REMOVE a(i,i) AFTER RENORM
|  |                xtem = x(j) + omega_l*xtem               ! REMOVE a(i,i) AFTER RENORM
|  |                xtem = max(xtem,0.0)                     ! apply constraints
```

```
              dimax = max(dimax,abs(xtem-x(j))       )
              xmax  = max( xmax,xtem)         ! for scaling epsilon
              x(j)  = xtem
        < end do dimax = dimax/xmax                 ! if xmax = 0, its broken anyway if (ldebug >= 3)
        &  write (*,'(a,i5,f8.4,8f8.5)') ' ',iter,dimax,(x(j),j=1,numj)

if (dimax <= epsilon) then
                go to 999
          < end if
        < end do write(*,8)'***LINITER: possible non-convergence',maxiter,dimax
        8 format (1x,a,i5,f18.10)

!     transfer on normal convergence
    999 continue
    !     ----------------------------------------------------
    !     un-do matrix scaling:
        do j=1,n
           b(j) = b(j) / scale(j)
           do i=1,n
              a(i,j) = a(i,j) / (scale(i)*scale(j))
           < end do
        < end do call traceflow (2,'LINITER')

return
        end
```

```
            subroutine make_centers (numiso_in)

use xray parameter (epsilon = 0.1)   ! in millimeters
            parameter (omega_c = 1.0)
            parameter (maxiter = 50)
            parameter (sq_epsilon = epsilon*epsilon)

*           -------------------------------------------- real*4   sum_x(numiso_in)    ! sum of closest x's
            real*4   sum_y(numiso_in)    ! sum of closest y's
            real*4   sum_z(numiso_in)    ! sum of closest z's
            real*4   volum(numiso_in)    ! volume of points in sum real*4   rdmax(numiso_in)    ! max radius
            real*4   sumsq(numiso_in)    ! rms radius
            real*4   stdev(numiso_in)    ! standard deviation
            real*4   shape(numiso_in)    ! shape parameter integer*4 maxpt(numiso_in)   ! # of point in cluster
                                         ! which is furthest from center parameter   ( max_hist=40)
            real*4    hist(0:max_hist,numiso_in)! cumulative radial histogram call traceflow (1,'MAKE_CENTERS')

C========================================================================== newcenter = .true.

if (allocated(centers)) deallocate (centers)
            allocate (centers(numiso_in))

numiso = 1 centers(numiso)%x0 = point(numiso)%x
            centers(numiso)%y0 = point(numiso)%y
            centers(numiso)%z0 = point(numiso)%z
        1   continue
+--------------> do iter=1,maxiter
|       CXXX    write (*,*) ' ITER = ',iter    !DEBUG
|               sq_change = 0.0        ! for convergence test
|
+--------------> do iso=1,numiso
|       CXXX    write (*,*) ' ISO = ',iso    !DEBUG
|               sum_x(iso) = 0.0
|               sum_y(iso) = 0.0
|               sum_z(iso) = 0.0
|               volum(iso) = 0.0
|               rdmax(iso) = 0.0
|               sumsq(iso) = 0.0
+--------------> do ihist = 0,max_hist
|                   hist(ihist,iso) = 0.0
+--------------< end do
+--------------< end do CXXX    write (*,*) ' NUM_PTS =',num_pts   !DEBUG +--------------> do ipt=1,num_pts      ! for each data point:
|               if (point(ipt)%tclass /= tumor) cycle
|               x0 = point(ipt)%x
|               y0 = point(ipt)%y
|               z0 = point(ipt)%z
|               vol0= point(ipt)%volume

|               dminsq = 1.0e20
```

```
+----------------> do iso = 1,numiso        ! for each iso-center:
|     CXXX              write (*,*) ' ISO = ',iso ! DEBUG
|                       distsq = (x0-centers(iso)%x0)**2 +
|          &                     (y0-centers(iso)%y0)**2 +
|          &                     (z0-centers(iso)%z0)**2
| +--------------> if (dminsq >= distsq) then       ! pick closest seed point
| I                      dminsq = distsq
| I                      isomax = iso
| +--------------< end if
+----------------< end do sum_x(isomax) = sum_x(isomax) + x0 * vol0
                   sum_y(isomax) = sum_y(isomax) + y0 * vol0
                   sum_z(isomax) = sum_z(isomax) + z0 * vol0 volum(isomax) = volum(isomax) + vol0 radius_sq    = dminsq
      C###                        (x0-centers(isomax)%x0)**2 +
      C### &                      (y0-centers(isomax)%y0)**2 +
      C### &                      (z0-centers(isomax)%z0)**2 sumsq(isomax) = sumsq(isomax) + radius_sq * vol0

C            ACCUMULATE HISTOGRAM:
                   iradius = min(nint(sqrt(radius_sq)),max_hist)
                   hist(iradius,isomax) = hist(iradius,isomax) + 1.0

+----------------> if (rdmax(isomax) < radius_sq) then
I                      rdmax(isomax) = radius_sq
I                      maxpt(isomax) = ipt
+----------------< end if
+---------------< end do +---------------> do iso = 1,numiso
|     CXXX              write (*,*) ' LOOP 2: ISO = ',iso,volum(iso)  !DEBUG
|                       if (volum(iso) <= 0.0) cycle     ! don't update point xnew = sum_x(iso)/volum(iso)
                   ynew = sum_y(iso)/volum(iso)
                   znew = sum_z(iso)/volum(iso)

dx  = xnew - centers(iso)%x0
                   dy  = ynew - centers(iso)%y0
                   dz  = znew - centers(iso)%z0 sq_change = max( sq_change, dx2 + dy2 + dz**2)

stdev(iso) = sqrt( sumsq(iso) /volum(iso) )

shape(iso) = ( stdev(iso)/(0.8*pi) )**0.6 /
       *                        ---------------------------       VERIFY
                &                 (volum(iso)/(1.333333*pi))

shape(iso) = (4./3.) * pi * stdev(iso)**3 /
       *                        ---------------------------       VERIFY
                &                       volum(iso)

C########## shape(iso) = 10.0*(shape(iso)-1.0)         ! map 1 >--> 0
                   rdmax(iso) = sqrt(rdmax(iso))

centers(iso)%x0 = centers(iso)%x0 + omega_c*dx
                   centers(iso)%y0 = centers(iso)%y0 + omega_c*dy
                   centers(iso)%z0 = centers(iso)%z0 + omega_c*dz
                   centers(iso)%radius_max = rdmax(iso)
+---------------< end do

C=========================================================
```

```
<=====<<<<          if (sq_change < sq_epsilon) go to 899
+-------------< end do write (*,*) ' ** POSSIBLE NON-CONVERGENCE IN CLUSTER **'

*   ------------------------
            899 continue

CXXX write (*,*) "???",numiso,isomax  ICXXX WHAT IS THE DIFFERENCE ?

call show_iso_hist (hist,max_hist,numiso,rdmax,stdev,shape)

+------------> if (numiso >= numiso_in) then  ! escape
|                  radmax = 0.0
|                  stdmax = 0.0
|+-----------> do iso = 1,numiso
||                 radmax = max(radmax,rdmax(iso))
||                 stdmax = max(stdmax,stdev(iso))
|+-----------< end do
<=====<<<<          go to 999   ! return
+-------------< end if

*   find and split largest cluster:
                rmax = 0.0
                isomax = 1                            ! new use of ISOMAX
+------------> do iso = 1,numiso                      ! find largest cluster
|+-----------> if (rmax < stdev(iso)) then            ! w.r.t. stdev (or rdmax)
||                 rmax = stdev(iso)
||                 isomax = iso
|+-----------< end if
+-------------< end do

*   add new seed point and re-solve: furthest point from center of cluster
                numiso = numiso +1
                centers(numiso)%x0 = point(maxpt(isomax))%x
                centers(numiso)%y0 = point(maxpt(isomax))%y
                centers(numiso)%z0 = point(maxpt(isomax))%z <=====<<<<          go to 1
            !   ------------------------------------------------
            999 continue
                call traceflow (2,'MAKE_CENTERS')
<=====<<<<          return end
```

```
************************************************************
        subroutine cone_shape ()
!       define the beam shape component as a cone use xray CXXX    real*4    x(0:30) = (/ (float(i),i=0,30)
CXXX    real*4    y(0:30)

call traceflow (1,'CONE_SHAPE')

*       ------------------------------------------------
        sigma = 3.7 / 2.0   !CXXX###??? apparent factor of 2 error vs data !!! ???

*       BUILD CONE MASK FOR EACH BEAM:
        do j=1,numbeam
            size_or_factor = beam(j)%conesize
            if (size_or_factor >= 2.0) then
                conesize = size_or_factor          ! USER INPUT CONE RADIUS
            else
                conesize = size_or_factor *
     &                    beam(j)%radius_max       ! SCALE FACTOR
            end if do kx=-max_grid,max_grid
                do ky = -max_grid,max_grid
                    radius_grid = sqrt(float(kx*kx + ky*ky))
                    radius_mm   = radius_grid
                    beam_shape(j)%grid(kx,ky)
     &                    = perror((radius_mm-(conesize+1.5))/sigma)
                < end do
            < end do
        < end do C  ------------------------------------------------
CXXX    print / plot beam pattern for verification debug
CXXX    do i=0,30
CXXX       y(i) = perror ( (x(i)- (conesize+1.5)) / sigma )
CXXX    end do
CXXX    call xyplot (x(0),y(0),31, 'radius', 'beam strength',' ',10.,5.)

if (ldebug >= 3) then
            do k=1,1
                write (*,*) 'CONE:'
                do j=-max_grid,max_grid
                    write (*,'(1x,40i1)')
     &                  (nint(10.0 * beam_shape(k)%grid(i,j)),
     &                       i=-max_grid,max_grid)
                < end do
            < end do
        < end if
        C  ------------------------------------------------ call traceflow (2,'CONE_SHAPE')

<=====<<<<   return
             end
```

```
*************************************************************************
         subroutine dvhist (hist,nh,tissue_type)

use xray real*4            hist(0:nh)
         integer*1         tissue_type call traceflow (1,'DVHIST')

hist = 0.0

+------------> do ipt=1,num_pts
|+---------------> if (point(ipt)%tclass == tissue_type) then
||                   idose= point(ipt)%dose * 100.0
||                   idose= max(idose, 0)
||                   idose= min(idose,nh)
||                   hist(idose) = hist(idose) + point(ipt)%volume
|+---------------< end if
+------------< end do call traceflow (2,'DVHIST')

<=====<<<<   return
             end
```

```
*************************************************************************
          subroutine cumhist (h,n)

real*4   h(n)

call traceflow (1,'CUMHIST')

+------------> do i=n-1,1,-1
|                h(i) = h(i) + h(i+1)
+------------< end do total = max(h(1),1.0)    ! SAFE ON DIVIDE BY ZERO !!!!
                                   ! e.g. if no AVOID areas, total == 0.0
+------------> do i=1,n
|                h(i) = 100.0 * h(i)/total
+------------< end do call traceflow (2,'CUMHIST')

<=====<<<<   return
             end
```

```
***************************************************************
       subroutine traceflow (flag,sub_name)
       use xray, only: ldebug integer*4    :: flag
       character*(*) :: sub_name character*2  :: symb = '--'
       integer*4    :: level = -1

<=====<<<      if (.not.(ldebug >= 1)) return if (flag == 1) level = level + 1
       if (flag == 1) symb  = '--'
       if (flag == 2) symb  = '..' write (*,*) (symb,i=0, min(max(level, 0),72)),sub_name if (flag == 2) level = level - 1

<=====<<<      return
       end
```

```
**********************************************************
              function perror(x)

c calculates the fraction of a normal curve falling above
      c "x" standard deviations above the mean:

real*4 perror,x,c,r
              real*4 derfdx,dx,p,a1,a2,a3,a4,a5
              real*4 eta,eta2,eta3,eta4,eta5 c dividing x by sqrt(2) makes the argument in units of standard deviatio
      c the new value of c normalizes the curve to an area of 1 data r  / 0.7071 0678    /
      c       data c  / 1.1283 791    0/
              data c  / 0.5641 8958    /
              data p  / 0.3275 911     /
              data a1 / 0.2258 3684 6 0/
              data a2 /-0.2521 2866 8 0/
              data a3 / 1.2596 9513 0 0/
              data a4 /-1.2878 2245 3 0/
              data a5 / 0.9406 4607 0 0/ dx= abs(r * x)

derfdx=c* exp(-dx*dx)

eta = 1. 0/(1. 0+p*dx)
              eta2=eta*eta
              eta3=eta*eta2
              eta4=eta*eta3
              eta5=eta*eta4 perror = (a1*eta+a2*eta2+a3*eta3+a4*eta4+a5*eta5)*derfdx
              if (x < 0.) perror=1.-perror <=====<<<<    return
              end

*===========================================================
              subroutine show_sordata (grid,flag,m,k)
              use xray, only: ldebug real*4    grid(-m:m,-m:m)
              logical*1 flag(-m:m,-m:m)

real*4, parameter :: epsilon = 0.1 character g(-m:m),f(-m:m)

<=====<<<<    if (.not.(ldebug >=4)) return write (*,*) "sor population statistics"
              num_zero = 0
              num_non  = 0
              num_true = 0
              num_false= 0
+--------------> do j=-m,m
|+--------------> do i=-m,m
||+----------------> if (abs(grid(i,j)) < epsilon) then
||                       num_zero = num_zero + 1
||                       g(i) = '0'
|+----------------= else
||                       num_non  = num_non + 1
|+----------------> if (grid(i,j) > 0.0) then
||                       g(i) = '+'
|+----------------= else
||                       g(i) = '-'
|+----------------< end if
|+----------------< end if
|+----------------> if (    flag(i,j)       ) then
```

```
|[                         num_true  = num_true + 1
|[                         f(i) = 'T'
|+---------------= else
|[                         num_false = num_false+ 1
|[                         f(i) = 'F'
|+---------------< end if
+---------------< end do
                 write (*,*) g,' ',f
+---------------< end do
                 total = num_zero + num_non
                 write (*,"(a,i4,2x,2i6,2x,2i6,i8)")
               &  ' ITER ',k,num_zero,num_true,num_non,num_false,nint(total)
                 pause <=====<<<<       return
                 end

*===========================================================
                 subroutine show_beam_depth (grid,m,k)
                 use xray, only: ldebug real*4   grid(-m:m,-m:m)

real*4, parameter :: epsilon = 0.1

<=====<<<<       if (.not.(ldebug >=4)) return

CXXX       write (*,*) "BEAM DEPTH POPULATION STATISTICS"
                 num_zero = 0
                 num_non  = 0
+--------------> do j=-m,m
|+-------------->  do i=-m,m
||+-------------> if (abs(grid(i,j)) < epsilon) then
||                     num_zero  = num_zero + 1
|+---------------= else
||                     num_non   = num_non  + 1
|+---------------< end if
|+--------------< end do
                 write (*,"(1x,79i1)")
             &       (nint(grid(i,j)),i=-m,m)
+--------------< end do
                 total = num_zero + num_non
                 write (*,"(a,4i6,2f8.3)") ' Beam ',k,num_zero,num_non,
             & nint(total),float(num_zero)/total,float(num_non)/total <=====<<<<       return
                 end

*===========================================================
                 subroutine show_points ()
                 use xray integer*4  num(air:avoid)

<=====<<<<       if (.not.(ldebug >=3)) return num = 0 write (*,*) "number of sampled points = ",num_pts

+--------------> do i=1,num_pts
                 k = point(i)%tclass
|+--------------> if (air <= k .and. k <=avoid) then
|                     num(k) = num(k) + 1
|+---------------= else
|                     write (*,*) " unknown tissue type:",k," point(",i,")"
|+---------------< end if
+--------------< end do
                 write (*,'(" Number of ",a6," points :",i6)') "air    ",num(air )
```

```
                    write (*,'(" Number of ",a6," points :",i6)') "bolus ",num(bolus)
                    write (*,'(" Number of ",a6," points :",i6)') "normal",num(norml)
                    write (*,'(" Number of ",a6," points :",i6)') "dense ",num(dense)
                    write (*,'(" Number of ",a6," points :",i6)') "tumor ",num(tumor)
                    write (*,'(" Number of ",a6," points :",i6)') "avoid ",num(avoid)

write (*,*) "number of sampled points = ",num_pts,sum(num)

<=====<<<<          return
                    end

*===========================================================
                    subroutine show_matrix (a,m,n,title)
                    use xray, only: ldebug real*4      a(m,n)
                    character*(*) title <=====<<<<          if (.not.(ldebug >=3)) return limit = min(m,13)

write (*,*) title
                    write (*,1000) (i,i=1,limit)
+------------->  do j=1,n
|                      write (*,2000) a(j,j),j,(a(i,j),i=1,limit)
+-------------< end do write (*,*) ' '

1000 format (' DIAG  J',14i5 )
               2000 format (1x,f5.2,i3 ,14f5.2)
<=====<<<<          return
                    end

*===========================================================
                    subroutine show_iso_hist (hist,nh,num,rdmax,stdev,shape)
                    use xray real*4      hist(0:nh,num)

real*4      rdmax(num)
                    real*4      stdev(num)
                    real*4      shape(num)

<=====<<<<          if (.not.(ldebug >=3)) return write (*,*) '--------------------------------------------'
                    write (*,"(3x,a,i3)") 'ISO-CENTER INFORMATION: NUM =',num
                    write (*,'(a,10f8.1)')' SHAPE',(shape(k),k=1,numiso)
                    write (*,'(a,10f8.1)')' RDMAX',(rdmax(k),k=1,numiso)
                    write (*,'(a,10f8.1)')' STDEV',(stdev(k),k=1,numiso)
                    write (*,'(a,10f8.1)')'   X  ',(centers(k)%x0,k=1,numiso)
                    write (*,'(a,10f8.1)')'   Y  ',(centers(k)%y0,k=1,numiso)
                    write (*,'(a,10f8.1)')'   Z  ',(centers(k)%z0,k=1,numiso)
                    write (*,*) ' '
                    write (*,"(3x,a,i3)") 'ISO-CENTER RADIUS HISTOGRAM: NUM =',num
+------------->  do i=0,nh
|                      write (*,"(2x,i4,3f8.1)") i,(hist(i,iso),iso=1,num)
+-------------< end do <=====<<<<          return
                    end

*===========================================================
                    subroutine show_hist (hist_tumor,hist_norml,hist_avoid,nh)
                    use xray, only: ldebug real*4      hist_tumor(0:nh)
```

```
              real*4  hist_norml(0:nh)
              real*4  hist_avoid(0:nh)

<=====<<<<    if (.not.(ldebug >=0)) return write (*,"(5x,3a8)") 'TUMOR','NORMAL','AVOID'
+------------> do i=0,nh
|                write (*,"(1x,i4,3i8)") i,
|             &    nint(hist_tumor(i)),nint(hist_norml(i)),nint(hist_avoid(i))
+------------< end do <=====<<<<    return
              end

*===========================================================================
              subroutine show_beams
              use xray <=====<<<<    if (ldebug < 1) return write (*,*)
              & '  # BEAM  ISO    WEIGHT    XO     YO     ZO  ',
              & 'RAD  CONE  TABLE  GANTRY'

+------------> do i=1,numbeam
|                write (*,9) i,
|             &              beam(i)%number,beam(i)%isocenter,
|             &              beam(i)%weight,
|             &              beam(i)%x0,beam(i)%y0,beam(i)%z0,
|             &              beam(i)%radius_max,beam(i)%conesize,
|             &              beam(i)%table_angle,beam(i)%gantry_angle
+------------< end do
              9 format (1x,3i5,f10.4,3f6.1,f5.1,f5.2,2f8.1)

<=====<<<<    return
              end

*===========================================================================
              subroutine show_atten
              use xray <=====<<<<    if (.not.(ldebug >=2)) return write (*,*) " attenuation index histogram:"
+------------> do i=min_atten,max_atten
|                write (*,"(1x,i6,i8)") i,num_atten(i)
+------------< end do num_atten = 0   ! re-zero histogram
<=====<<<<    return
              end
```

```
          subroutine calc_voxel_dose (dose_file)
          use xray integer      :: ttype,tissue
          integer*2    :: vox character*(*)  :: dose_file character, allocatable :: d(:,:,:)

character    :: c0 c0 = char(0)

*         --------------------------------------------------
          call traceflow (1,'CALC_VOXEL_DOSE')

if (allocated(d)) deallocate (d)
             allocate (d(ilo:ihi,jlo:jhi,klo:khi))

numx = ihi - ilo + 1
          numy = jhi - jlo + 1
          numz = khi - klo + 1

<=====<<<< if (ldebug < 1) go to 999 if (ldebug >=1) write (*,*)'ALLOCATED DOSE ARRAY',numx,numy,numz

+-------------> do k=klo,khi
                   if (ldebug >= 1) write (*,*) ' SLICE:',k
+--------------> do j=jlo,jhi
+----------------> do i=ilo,ihi
                   vox   = voxel(i,j,k)
                   tissue = abs(vox)
                   ttype = tissues(tissue)%tclass
                                  ! CATEGORIZE ALL TISSUE AS
                                  ! AIR,BOLUS,NORML,DENSE,AVOID,TUMOR
+--------------------> if (ttype == air ) then
|                         d(i,j,k) = c0
|                         cycle
+--------------------< end if xx = float(i-ilo) * xthick + xlo
                   yy = float(j-jlo) * ythick + ylo
                   zz = float(k-klo) * zthick + zlo dose = 0.0

+--------------------> do jbeam=1,numbeam

*              find coordinates relative to iso-center
                     x1 = xx - beam(jbeam)%x0
                     y1 = yy - beam(jbeam)%y0
                     z1 = zz - beam(jbeam)%z0

*              project to beam coordinates
                     x2 = beam(jbeam)%a*x1 +
         &              beam(jbeam)%b*y1 +
         &              beam(jbeam)%c*z1
                     y2 = beam(jbeam)%d*x1 +
         &              beam(jbeam)%e*y1 +
         &              beam(jbeam)%f*z1
                     z2 = beam(jbeam)%g*x1 +
         &              beam(jbeam)%h*y1 +
         &              beam(jbeam)%i*z1

*              correct lateral coordinates for beam spread:
                     factor = (arc_radius-z2) / arc_radius  !C### VERIFY SIGN !!!
                     i2 = nint(x2 / factor)
                     j2 = nint(y2 / factor)
```

```
   +--------------------> if (abs(i2)<=max_grid .and. abs(j2)<=max_grid) then
   |
   |                         nindex = nint(beam_depth(jbeam)%grid(i2,j2)-z2 )
   |
   I+--------------------> if (nindex < min_atten) then
   II                         nindex = min_atten
   I+-----------------------= else
   II                         nindex = min(nindex,max_atten)
   I+-----------------------< end if
   I
   I                         dose = dose + beam(jbeam)%weight             *
   I       &                          beam_shape(jbeam)%grid(i2,j2)   *
   I       &                          atten(nindex) / factor**2 ! spherical spreading
   +--------------------< end if
   +-----------------< end do
                  ! 110% full scale + 1 so 0% doesn't map into air:
                  ijkdose = nint(dose*255.0 / 1.20 ) + 1
                  ijkdose = min(ijkdose,255)
                  ijkdose = max(ijkdose,  0)
                  d(i,j,k) = char(ijkdose)
   +-----------------< end do
   +---------------< end do if (ldebug >=2 ) write(*,*)' DOSE Calculation Slice:',k
         C##PIX_OUT BMP   if (LDEBUG >=3 ) call pix_out (d,k)
   +-------------< end do call dose_out (dose_file,d)

deallocate (d)

999 call traceflow (2,'CALC_VOXEL_DOSE')

<=====<<<<    return
              end
```

40

```
***********************************************************************
         subroutine outcat (out,in,ext)

character*(*) out,in,ext

+--------------> do i=len(in),2,-1
|+--------------> if (in(i:i) == '.') then
||                   out = in(1:i-1) // ext
<=====<<<<           return                    ! NORMAL RETURN
|+---------------< end if
+---------------< end do write (*,*) ' OUTCAT FAILED',out,in,ext out = 'TEM_FILE.DAT'

<=====<<<<    return
         end
```

```
*************************************************************
          subroutine iswap (i,j)
          integer*4  i,j,k k = i
          i = j
          j = k <=====<<<<   return
          end
```

```
*******************************************************************
        subroutine pix_out (d,k)
        use xray character    ::  d(ilo:ihi,jlo:jhi,klo:khi)
        character    ::  b(ilo:ihi,jlo:jhi)

character*12 ::  pixfile pixfile      = 'PIXF0000.BMP'
        pixfile(1:4) = inputfile(1:4)

mm = ihi-ilo+1
        nn = jhi-jlo+1 b = char(voxel(:,:,k))
        call sequence_name (pixfile,k)
        call bmp_pix (b(ilo,jlo),d(ilo,jlo,k),mm,nn,pixfile)

<=====<<<<   return
        end
```

```
***********************************************************************
          subroutine sequence_name (f,k)

character*(*) f idot = index(f,'.')

i2 = idot-1
          i1 = i2 - 3
          write (f(i1:i2),'(i4)') k

+------------> do i=i1,i2
|                 if (f(i:i) .eq. ' ') f(i:i) = '0'
+------------< end do write (*,*) 'SEQUENCE: ',f
<=====<<<< return
          end
```

Appendix C
Source Code Defining Parameters Used by the Various Subroutines

```
module xray
save real*4    , parameter :: PI = 3.141592653589793
real*4    , parameter :: D2R= PI / 180.0              ! DEGREES TO RADIANS
real*4    , parameter :: R2D= 180.0 / PI              ! RADIANS TO DEGREES real*4    , parameter :: ARC_RADIUS = 1000.0          ! IN MM integer*4, parameter :: MAX_GRID = 19                 ! DIMENSION OF BEAM SHAPE & BEAM DEPTH ARRAYS integer*1, parameter :: AIR  =0                       !
integer*1, parameter :: BOLUS=1                       ! DEFINE CODES FOR THE VARIOUS TISSUE TYPES
integer*1, parameter :: NORML=2                       ! AS WELL AS THEIR "PRIORITY ORDER"
integer*1, parameter :: DENSE=3                       ! WHICH CONTROLS WHICH TYPE IS ASSIGNED
integer*1, parameter :: TUMOR=4                       ! IN THE CASE OF OVERLAPPING DESIGNATIONS
integer*1, parameter :: AVOID=5                       !

integer*4, parameter ::           MIN_ATTEN =  -50 ! enough to span tissue
integer*4, parameter ::           MAX_ATTEN =  300 ! enough to span tissue
real*4      tab_atten(min_atten:max_atten)         ! attenuation function
integer*4:: num_atten(min_atten:max_atten)

integer*4           :: LDEBUG = 3                  ! 0 = none
! OPTIONS FOR EXTRA INFORMATION                    ! 1 = subroutine flow & dense dose file
! IN OUTPUT STREAM                                 ! 2 = depth array
                                                   ! 3 = internal printouts, BMP of Slices
                                                   ! 4 = LOTS OF DETAIL

*       --------------------------------------------------------------------
    type xray_point
        sequence
        real*4    x         ! x coordinate of voxel
        real*4    y         ! y coordinate of voxel
        real*4    z         ! z coordinate of voxel
        real*4    volume    ! volume represented by decimated voxel in mm^3
        real*4    dose      ! calculated 1 mm^3 dose for this voxel
        real*4    sigma     ! relative dosage tolerance within tissue class
        integer*2 index     ! into tissue info array
        integer*1 tclass    ! AIR, BOLUS, NORML, TUMOR, AVOID
        integer*1 isocenter ! iso-center in which point belongs
    end type

*       --------------------------------------------------------------------
    type xray_boundary
        sequence
        real*4    x
        real*4    y
        real*4    z
    end type

*       --------------------------------------------------------------------
    type xray_beam
        sequence
        integer*4 number          ! used to lock beams in an arc
        integer*4 isocenter       ! iso-center of current beam real*4    x0              ! iso_center
        real*4    y0              ! iso_center
        real*4    z0              ! iso_center real*4    radius_max      ! maximum radius for current iso-center
        real*4    conesize        ! ( < 0.0  implies SILHOUETTE )
        real*4    weight          ! optimized beam weight real*4    table_angle     ! degrees
```

1

```
        real*4      gantry_angle    ! degrees
        real*4      collim_angle    ! degrees real*4      a               ! element of transform matrix
        real*4      b               ! element of transform matrix
        real*4      c               ! element of transform matrix
        real*4      d               ! element of transform matrix
        real*4      e               ! element of transform matrix
        real*4      f               ! element of transform matrix
        real*4      g               ! element of transform matrix
        real*4      h               ! element of transform matrix
        real*4      i               ! element of transform matrix
      end type

*     ----------------------------------------------------------------
      type xray_grid
!       SEQUENCE
        real*4   grid(-max_grid:max_grid,-max_grid:max_grid)
      end type

*     ----------------------------------------------------------------
      type xray_center
        sequence
          real*4    x0              ! iso_center
          real*4    y0              ! iso_center
          real*4    z0              ! iso_center
          real*4    radius_max      ! mm
      end type

*     ----------------------------------------------------------------
      type xray_tissues
        sequence
          real*4    sigma     ! intended relative sigma within tissue class
          integer*2 tclass    ! AIR, BOLUS, NORML, TUMOR, or AVOID
          integer*2 reserved  ! structures take multiple of 4/8 bytes anyway
      end type !     ----------------------------------------------------------------
!     GLOBALS character*24                        :: inputfile logical                             :: newpoints = .true.
      logical                             :: newbeams  = .true.
      logical                             :: newcenter = .true.

real*4                              :: xthick ,ythick ,zthick
      real*4                              :: xlo    ,ylo    ,zlo
      integer*4                           :: ilo,ihi,jlo,jhi,klo,khi integer*2        , allocatable   :: voxel(:,:,:)

integer*4                           :: numbeam
      integer*4                           :: maxb   ! max beam # for locking arcs
      type (xray_beam)  , allocatable   :: beam        (:)
      type (xray_grid)  , allocatable   :: beam_depth(:)
      type (xray_grid)  , allocatable   :: beam_shape(:)

integer*4                           :: num_pts
      type (xray_point) , allocatable   :: point       (:)

integer*4                           :: numboundary
      type (xray_boundary), allocatable :: boundary    (:)

integer*4                           :: numiso
      type (xray_center) , allocatable  :: centers     (:)

integer*4                           :: maxtypes
      type (xray_tissues) , allocatable :: tissues     (:)

end module
```

What is claimed is:

1. A method for optimizing delivery of radiation to the body of a patient admitted for oncology treatment or for stereotactic radiosurgery of a tumor comprising the steps of:

introducing radiation into said body from multiple directions with the beams intersecting at the tumor;

varying the intensities of radiation as a function of angle; and optimizing by constrained matrix inversion the optimum weights and dosage in the treatment of the tumor.

2. The method of claim 1, wherein the weight is assigned according to the tissue types of tumor, healthy and avoidance area.

3. A method for optimizing delivery of radiation to the body of a patient admitted for oncology treatment or for stereotactic radiosurgery of a tumor comprising the steps of:

introducing radiation into said body from multiple directions with the beams intersecting at the tumor;

varying the intensities of radiation as a function of angle;

optimizing with respect to $c_k$ in the following relationship:

$$\text{Cost} = \sum_{i=1}^{\text{Volume\_Elements}} w_i \cdot \left[ \left( \sum_{k=1}^{\text{Number\_of\_Beams}} c_k \cdot d_{i,k} \right) - m_i \right]^2$$

where the index i denotes the range of volume elements;

the index k denotes the range of beams;

$c_k$ is the relative weight of the k-th beam;

$m_i$ is the intended dose in volume element i;

$w_i$ is the weight with which the residual at point i is to be considered; and $d_{i,k}$ is the predicted dose at point i that would arrive only from a single unit strength beam number k.

4. The method of claim 3, wherein the weight $w_i$ is assigned according to the tissue types of tumor, healthy and avoidance area.

5. A method for optimizing delivery of radiation to the body of a patient admitted for oncology treatment or for stereotactic radiosurgery of a tumor comprising the steps of:

introducing radiation into said body from multiple directions with the beams intersecting at the tumor;

varying the intensities of radiation as a function of angle;

optimizing with respect to $c_k$ in the following relationship:

$$\text{Cost} = \sum_{i=1}^{\text{Volume\_Elements}} w_i \cdot \left[ \left( \sum_{k=1}^{\text{Number\_of\_Beams}} c_k \cdot d_{i,k} \right) - m_i \right]^2$$

where $c_k$ is the relative weight of the k-th beam and is constrained to be greater than or equal to zero;

the index i denotes the range of volume elements;

the index k denotes the range of beams;

$m_i$ is the intended dose in volume element i;

$w_i$ is the weight with which the residual at point i is to be considered; and $d_{i,k}$ is the predicted dose at point i that would arrive only from a single unit strength beam number k.

6. The method of claim 5, wherein the weight $w_i$ is assigned according to the tissue types of tumor, healthy and avoidance area.

7. A method for optimizing delivery of radiation to the body of a patient admitted for oncology treatment or for stereotactic radiosurgery of a tumor comprising the steps of:

introducing radiation into said body from multiple directions with the beams intersecting at the tumor;

varying the intensities of radiation as a function of angle;

optimizing by constrained matrix inversion the optimum weights and dosage in the treatment of the tumor; and solving for beam weight under the constraint that no beam weight is negative.

8. The method of claim 7, wherein the weight $w_i$ is assigned according to the tissue types of tumor, healthy and avoidance area.

9. The method of claim 7, including the step of automatically selecting multiple iso-centers.

* * * * *